(12) United States Patent
Chobotov et al.

(10) Patent No.: US 9,050,754 B2
(45) Date of Patent: Jun. 9, 2015

(54) ENDOVASCULAR GRAFT JOINT AND METHOD FOR MANUFACTURE

(75) Inventors: Michael V. Chobotov, Santa Rosa, CA (US); Patrick Stephens, Santa Rosa, CA (US)

(73) Assignee: TRIVASCULAR, INC., Santa Rosa, CA (US)

( * ) Notice: Subject to any disclaimer, the term of this patent is extended or adjusted under 35 U.S.C. 154(b) by 0 days.

(21) Appl. No.: 12/729,182

(22) Filed: Mar. 22, 2010

(65) Prior Publication Data

US 2010/0292770 A1 Nov. 18, 2010

Related U.S. Application Data

(60) Continuation of application No. 11/870,748, filed on Oct. 11, 2007, now Pat. No. 7,682,475, which is a continuation of application No. 10/640,368, filed on Aug. 13, 2003, now abandoned, which is a division of application No. 10/029,584, filed on Dec. 20, 2001, now Pat. No. 7,090,693.

(51) Int. Cl.
*A61F 2/07* (2013.01)
*B29C 65/18* (2006.01)
(Continued)

(52) U.S. Cl.
CPC ........... *B29C 65/18* (2013.01); *Y10T 156/1002* (2013.01); *A61F 2250/0028* (2013.01); *A61F 2002/075* (2013.01); *A61F 2210/0076* (2013.01); *B29C 53/44* (2013.01); *B29C 66/1122* (2013.01); *B29C 66/24* (2013.01);
(Continued)

(58) Field of Classification Search
CPC .................. A61F 2210/0076; A61F 2250/003; A61F 2/0009; A61F 2310/00005; A61F 2310/00389; A61F 2/07; A61F 2002/07; A61F 2002/072; A61F 2002/075; A61F 2002/077; A61F 2/12; B29K 2027/18; B29K 2227/18; B29K 2427/18; B29K 2627/18; B29K 2827/18; A61B 19/24
USPC ...................................... 623/1.13, 1.25, 23.67
See application file for complete search history.

(56) References Cited

U.S. PATENT DOCUMENTS 1,324,850 A 12/1919 Roberts
2,372,917 A 4/1945 Tuttle
(Continued)

FOREIGN PATENT DOCUMENTS

EP 0821648 B1 9/2001
EP 0808140 B1 12/2001
(Continued)

OTHER PUBLICATIONS

Haimovitch, L., and Patterson, N., "Robust growth is forecast for endovascular repair of AAAs," The BBI Newsletter, 26(5): 113-114 (May 2003).

(Continued)

*Primary Examiner* — Andrew Iwamaye
*Assistant Examiner* — Leslie Lopez
(74) *Attorney, Agent, or Firm* — Hoffmann & Baron, LLP

(57) ABSTRACT

A joint and method for producing a joint in an endovascular graft. In one embodiment, a flap of a flexible material portion of an endovascular graft is folded about a portion of an expandable member to form a loop portion. The flap is secured in the loop configuration so that tensile force on the expandable member is transferred into a shear force on the fixed portion of the flap.

15 Claims, 24 Drawing Sheets

(51) Int. Cl.
  B29C 53/44 (2006.01)
  B29C 65/00 (2006.01)
  *B29L 22/02* (2006.01)
  *B29L 31/00* (2006.01)
  *B29C 65/48* (2006.01)

(52) U.S. Cl.
  CPC ........... B29C 66/43 (2013.01); B29C 66/65 (2013.01); B29C 66/81422 (2013.01); *B29L 2022/02* (2013.01); *B29L 2022/022* (2013.01); *B29L 2031/7546* (2013.01); A61F 2/07 (2013.01); *A61F 2002/072* (2013.01); *A61F 2250/0003* (2013.01); *B29C 66/81812* (2013.01); *B29C 65/48* (2013.01); *B29C 65/4815* (2013.01); *B29C 65/483* (2013.01); *B29C 65/482* (2013.01); B29C 66/4322 (2013.01); B29C 66/438 (2013.01)

(56) References Cited

U.S. PATENT DOCUMENTS

| | | | |
|---|---|---|---|
| 2,983,961 A | | 5/1961 | Titterton et al. |
| 3,631,854 A | | 1/1972 | Fryer et al. |
| 3,991,767 A | * | 11/1976 | Miller et al. ............... 604/8 |
| 4,049,762 A | | 9/1977 | Martino et al. |
| 4,201,144 A | | 5/1980 | Manabe et al. |
| 4,218,420 A | | 8/1980 | Jacob et al. |
| 4,229,838 A | | 10/1980 | Mano |
| 4,319,872 A | | 3/1982 | Lupke et al. |
| 4,386,566 A | | 6/1983 | Moss |
| 4,580,568 A | | 4/1986 | Gianturco |
| 4,731,073 A | | 3/1988 | Robinson |
| 4,955,899 A | | 9/1990 | Della Corna et al. |
| 5,122,154 A | | 6/1992 | Rhodes |
| 5,156,620 A | | 10/1992 | Pigott |
| 5,197,976 A | | 3/1993 | Herweck et al. |
| 5,447,152 A | | 9/1995 | Kohsai et al. |
| 5,476,506 A | | 12/1995 | Lunn |
| 5,522,881 A | | 6/1996 | Lentz |
| 5,527,353 A | | 6/1996 | Schmitt |
| 5,529,653 A | | 6/1996 | Glastra |
| 5,556,414 A | | 9/1996 | Turi |
| 5,566,426 A | | 10/1996 | Lu |
| 5,607,478 A | | 3/1997 | Lentz et al. |
| 5,609,624 A | | 3/1997 | Kalis |
| 5,628,782 A | | 5/1997 | Myers et al. |
| 5,628,786 A | | 5/1997 | Banas et al. |
| 5,641,373 A | | 6/1997 | Shannon et al. |
| 5,653,745 A | | 8/1997 | Trescony et al. |
| 5,667,523 A | | 9/1997 | Bynon et al. |
| 5,700,285 A | | 12/1997 | Myers et al. |
| 5,713,917 A | | 2/1998 | Leonhardt et al. |
| 5,716,395 A | | 2/1998 | Myers et al. |
| 5,718,973 A | | 2/1998 | Lewis et al. |
| 5,735,892 A | | 4/1998 | Myers et al. |
| 5,769,885 A | | 6/1998 | Quiachon et al. |
| 5,782,909 A | | 7/1998 | Quiachon et al. |
| 5,789,047 A | | 8/1998 | Sasaki et al. |
| 5,800,512 A | * | 9/1998 | Lentz et al. ............... 623/1.1 |
| 5,871,538 A | | 2/1999 | Dereume |
| 5,931,865 A | | 8/1999 | Silverman et al. |
| 5,944,750 A | | 8/1999 | Tanner et al. |
| 5,957,973 A | | 9/1999 | Quiachon et al. |
| 5,961,545 A | | 10/1999 | Lentz et al. |
| 5,962,039 A | | 10/1999 | Katou et al. |
| 5,972,441 A | * | 10/1999 | Campbell et al. ............ 428/34.1 |
| 5,976,650 A | | 11/1999 | Campbell et al. |
| 5,993,489 A | | 11/1999 | Lewis et al. |
| 6,001,123 A | | 12/1999 | Lau |
| 6,004,348 A | | 12/1999 | Banas et al. |
| 6,025,044 A | | 2/2000 | Campbell et al. |
| 6,027,811 A | | 2/2000 | Campbell et al. |
| 6,121,042 A | | 9/2000 | Peterson et al. |
| 6,143,022 A | | 11/2000 | Shull et al. |
| 6,149,681 A | | 11/2000 | Houser et al. |
| 6,187,036 B1 | | 2/2001 | Shaolian et al. |
| 6,187,054 B1 | | 2/2001 | Colone et al. |
| 6,197,049 B1 | | 3/2001 | Shaolian et al. |
| 6,203,568 B1 | | 3/2001 | Lombardi et al. |
| 6,214,039 B1 | | 4/2001 | Banas et al. |
| 6,245,099 B1 | | 6/2001 | Edwin et al. |
| 6,245,100 B1 | | 6/2001 | Davila et al. |
| 6,264,686 B1 | | 7/2001 | Rieu et al. |
| 6,267,834 B1 | | 7/2001 | Shannon et al. |
| 6,280,467 B1 | | 8/2001 | Leonhardt |
| 6,287,330 B1 | | 9/2001 | Johansson et al. |
| 6,293,969 B1 | | 9/2001 | Chuter |
| 6,296,661 B1 | | 10/2001 | Davila et al. |
| 6,306,164 B1 | | 10/2001 | Kujawski |
| 6,312,458 B1 | | 11/2001 | Golds |
| 6,312,462 B1 | * | 11/2001 | McDermott et al. ......... 623/1.25 |
| 6,319,279 B1 | | 11/2001 | Shannon et al. |
| 6,322,587 B1 | | 11/2001 | Quiachon et al. |
| 6,336,937 B1 | | 1/2002 | Vonesh et al. |
| 6,344,054 B1 | * | 2/2002 | Parodi ..................... 623/1.13 |
| 6,344,055 B1 | | 2/2002 | Shukov |
| 6,357,104 B1 | | 3/2002 | Myers |
| 6,361,637 B2 | | 3/2002 | Martin et al. |
| 6,364,904 B1 | | 4/2002 | Smith |
| 6,368,347 B1 | | 4/2002 | Maini et al. |
| 6,391,052 B2 | | 5/2002 | Buirge et al. |
| 6,398,803 B1 | | 6/2002 | Layne et al. |
| 6,402,779 B1 | | 6/2002 | Colone et al. |
| 6,416,537 B1 | | 7/2002 | Martakos et al. |
| 6,425,855 B2 | | 7/2002 | Tomonto |
| 6,428,571 B1 | | 8/2002 | Lentz et al. |
| 6,432,131 B1 | | 8/2002 | Ravenscroft |
| 6,436,135 B1 | | 8/2002 | Goldfarb |
| 6,443,981 B1 | | 9/2002 | Colone et al. |
| 6,451,047 B2 | | 9/2002 | McCrea et al. |
| 6,451,050 B1 | | 9/2002 | Rudakov et al. |
| 6,454,796 B1 | | 9/2002 | Barkman et al. |
| 6,517,574 B1 | | 2/2003 | Chuter |
| 6,520,984 B1 | | 2/2003 | Garrison et al. |
| 6,523,576 B2 | | 2/2003 | Imaeda et al. |
| 6,524,336 B1 | | 2/2003 | Papazoglou et al. |
| 6,540,780 B1 | | 4/2003 | Zilla et al. |
| 6,547,814 B2 | | 4/2003 | Edwin et al. |
| 6,547,815 B2 | | 4/2003 | Myers |
| 6,554,858 B2 | | 4/2003 | Dereume et al. |
| 6,558,414 B2 | | 5/2003 | Layne |
| 6,579,314 B1 | | 6/2003 | Lombardi et al. |
| 6,582,458 B1 | | 6/2003 | White et al. |
| 6,652,570 B2 | | 11/2003 | Smith et al. |
| 2001/0023370 A1 | | 9/2001 | Smith et al. |
| 2001/0036522 A1 | | 11/2001 | Hanada et al. |
| 2001/0039446 A1 | | 11/2001 | Edwin et al. |
| 2001/0049550 A1 | | 12/2001 | Martin et al. |
| 2001/0053929 A1 | | 12/2001 | Vonesh et al. |
| 2002/0002397 A1 | | 1/2002 | Martin et al. |
| 2002/0019665 A1 | | 2/2002 | Dehdashtian et al. |
| 2002/0026231 A1 | | 2/2002 | Shannon et al. |
| 2002/0032408 A1 | | 3/2002 | Parker et al. |
| 2002/0040236 A1 | | 4/2002 | Lau et al. |
| 2002/0040237 A1 | | 4/2002 | Lentz et al. |
| 2002/0045931 A1 | | 4/2002 | Sogard et al. |
| 2002/0055768 A1 | | 5/2002 | Hess et al. |
| 2002/0065552 A1 | | 5/2002 | Jayaraman et al. |
| 2002/0099435 A1 | | 7/2002 | Stinson |
| 2002/0099436 A1 | | 7/2002 | Thornton et al. |
| 2002/0107561 A1 | | 8/2002 | Pinheiro |
| 2002/0111667 A1 | | 8/2002 | Girton et al. |
| 2002/0138129 A1 | | 9/2002 | Armstrong et al. |
| 2002/0156521 A1 | | 10/2002 | Ryan et al. |
| 2002/0169499 A1 | | 11/2002 | Zilla et al. |
| 2002/0173836 A1 | | 11/2002 | Pinchuk |
| 2003/0006528 A1 | | 1/2003 | Edwin et al. |
| 2003/0009211 A1 | | 1/2003 | DiCarlo |
| 2003/0009212 A1 | | 1/2003 | Kerr |

(56) References Cited

U.S. PATENT DOCUMENTS

| | | |
|---|---|---|
| 2003/0097174 A1 | 5/2003 | Henderson |
| 2003/0139806 A1 | 7/2003 | Haverkost et al. |

FOREIGN PATENT DOCUMENTS

| | | |
|---|---|---|
| EP | 0877582 B1 | 10/2002 |
| EP | 1148843 B1 | 4/2003 |
| WO | 9505277 A1 | 2/1995 |
| WO | 9624308 A1 | 8/1996 |
| WO | 9633066 A1 | 10/1996 |
| WO | 9727820 A1 | 8/1997 |
| WO | 9732714 A1 | 9/1997 |
| WO | 9838947 A1 | 9/1998 |
| WO | 9900073 A1 | 1/1999 |
| WO | 0042947 A2 | 7/2000 |
| WO | 0042948 A2 | 7/2000 |
| WO | 0045741 A1 | 8/2000 |
| WO | 0101886 A1 | 1/2001 |
| WO | 0101887 A1 | 1/2001 |
| WO | 0115633 A1 | 3/2001 |
| WO | 0121107 A1 | 3/2001 |
| WO | 0128456 A1 | 4/2001 |
| WO | 0152771 A1 | 7/2001 |
| WO | 0158384 A1 | 8/2001 |
| WO | 0167993 A2 | 9/2001 |
| WO | 0174270 A2 | 10/2001 |
| WO | 02100454 A1 | 12/2002 |
| WO | 03003946 A1 | 1/2003 |
| WO | 03026713 A1 | 4/2003 |
| WO | 03094795 A1 | 11/2003 |
| WO | 03094797 A1 | 11/2003 |
| WO | 03094799 A1 | 11/2003 |

OTHER PUBLICATIONS

Mennig, G., Mold-Making Handbook, (1998), Hanser/Gardner Publications, Inc., 2nd ed., pp. 252-253.

US 6,413,270, 07/2002, Thornton et al. (withdrawn)

\* cited by examiner

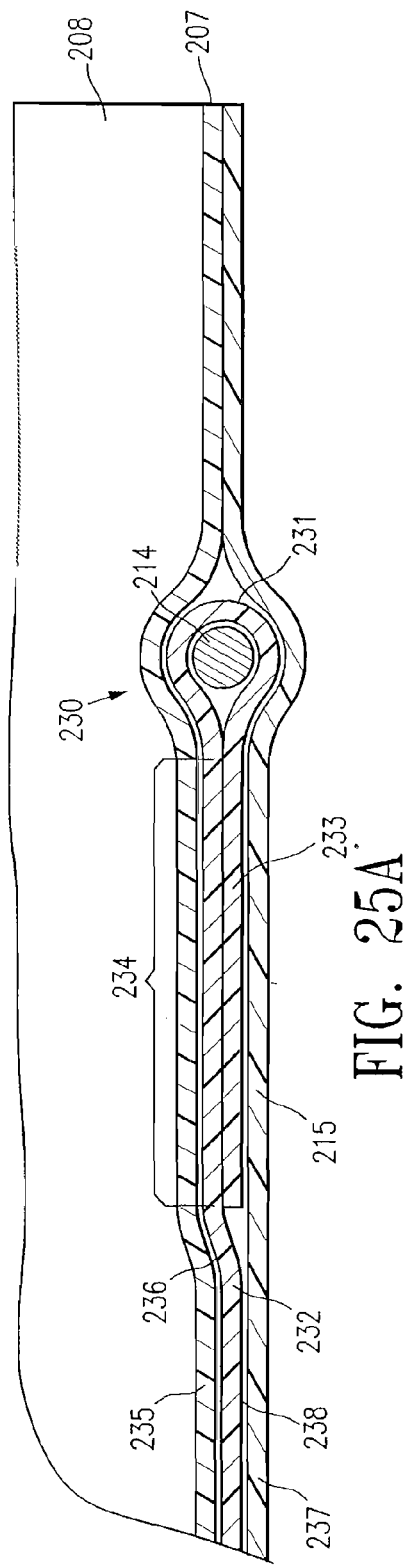
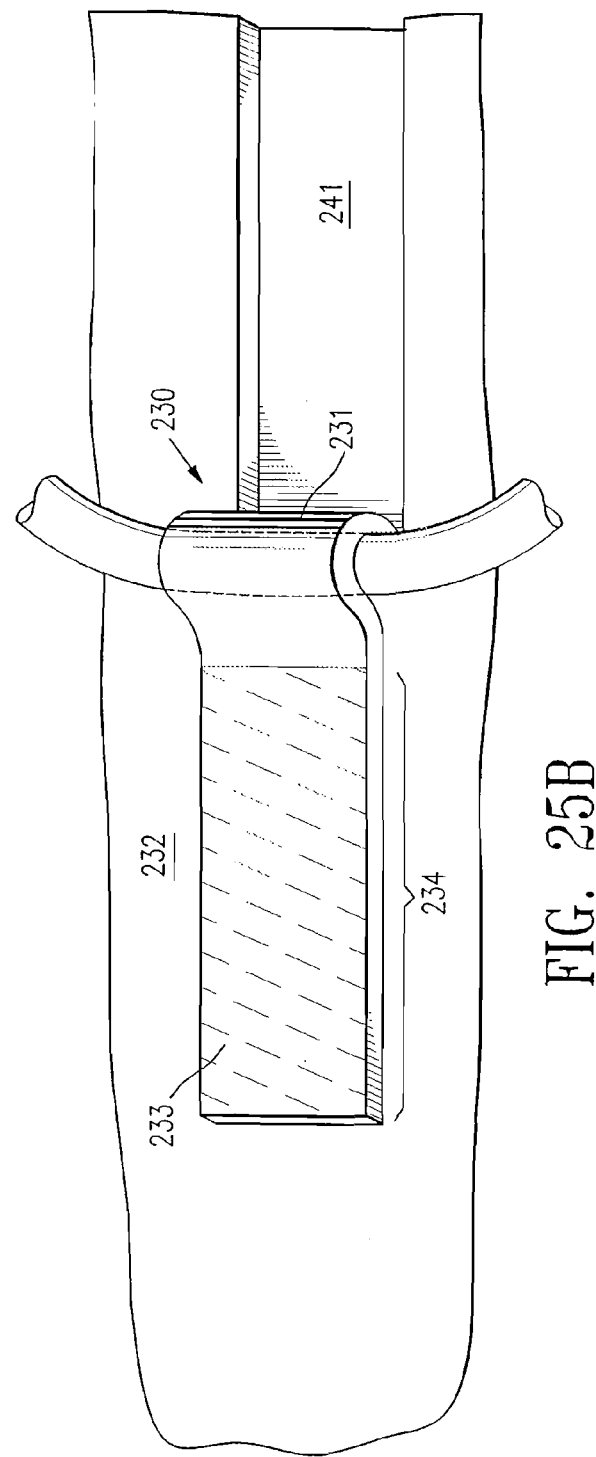
FIG. 25A
FIG. 25B

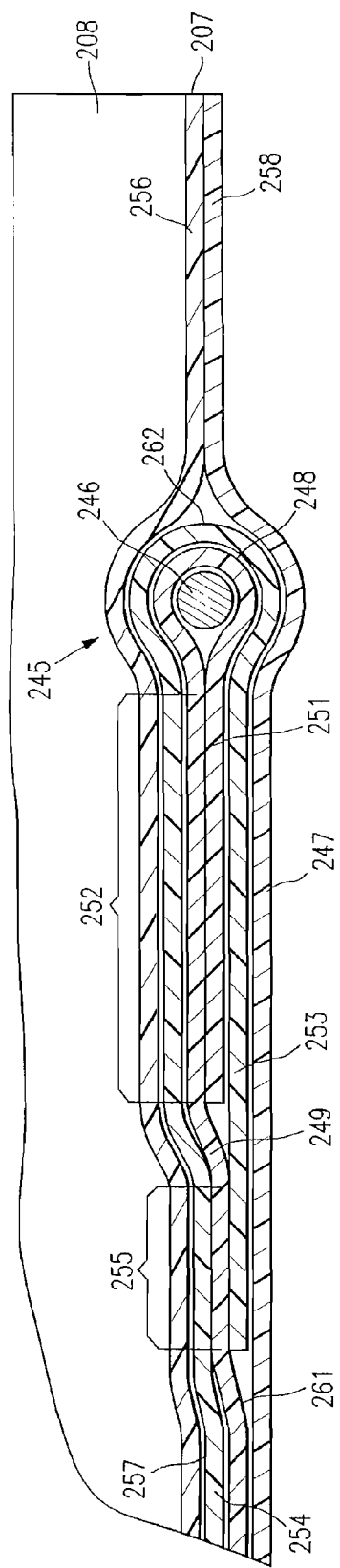
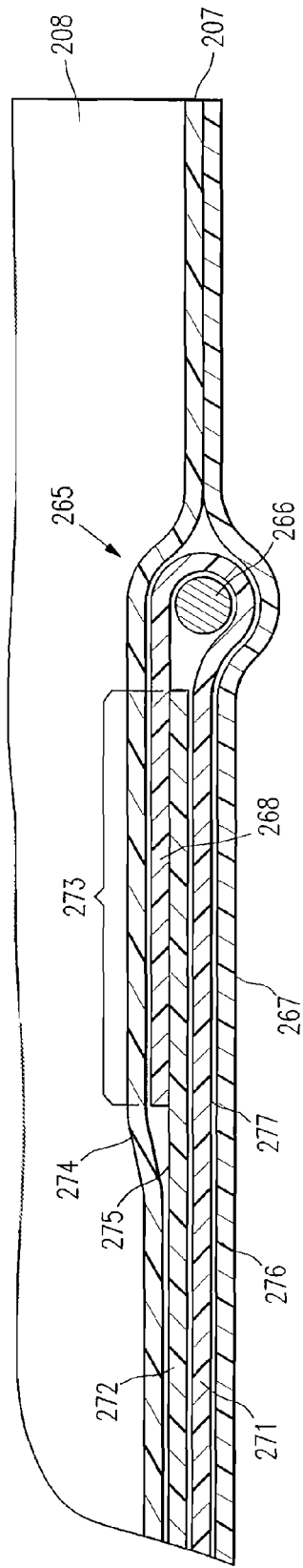
FIG. 26
FIG. 27

ENDOVASCULAR GRAFT JOINT AND METHOD FOR MANUFACTURE

CROSS-REFERENCE TO RELATED APPLICATIONS

This application is a continuation of U.S. patent application Ser. No. 11/870,748, filed Oct. 11, 2007, which is a continuation of U.S. patent application Ser. No. 10/640,368, filed Aug. 13, 2003, now abandoned, which is a divisional of U.S. patent application Ser. No. 10/029,584, filed Dec. 20, 2001, now U.S. Pat. No. 7,090,693, the contents of which are incorporated herein b reference.

RELATED TECHNOLOGY

This application is related in technology to U.S. patent application Ser. No. 10/029,570, filed Dec. 20, 2001, entitled "Method and Apparatus for Manufacturing an Endovascular Graft Section", by Chobotov et al., now U.S. Pat. No. 6,776,604, and to U.S. patent application Ser. No. 10/029,559, filed Dec. 20, 2001, entitled "Advanced Endovascular Graft", by Chobotov et al., now U.S. Pat. No. 7,147,661. All of the above applications are commonly owned and were filed on the same date. All of the above applications are hereby incorporated by reference, each in their entirety.

BACKGROUND

Embodiments of the device and method discussed herein relate to a system and method for manufacturing intracorporeal devices used to replace, strengthen, or bypass body channels or lumens of patients; in particular, those channels or lumens that have been affected by conditions such as abdominal aortic aneurysms.

Existing methods of treating abdominal aortic aneurysms include invasive surgical methods with grafts used to replace the diseased portion of the artery. Although improvements in surgical and anesthetic techniques have reduced perioperative and postoperative morbidity and mortality, significant risks associated with surgical repair (including myocardial infarction and other complications related to coronary artery disease) still remain.

Due to the inherent hazards and complexities of such surgical procedures, various attempts have been made to develop alternative repair methods that involve the endovascular deployment of grafts within aortic aneurysms. One such method is the non-invasive technique of percutaneous delivery of grafts and stent-grafts by a catheter-based system. Such a method is described by Lawrence, Jr. et al. in "Percutaneous Endovascular Graft: Experimental Evaluation", *Radiology* (1987). Lawrence et al. describe therein the use of a Gianturco stent as disclosed in U.S. Pat. No. 4,580,568 to Gianturco. The stent is used to position a Dacron® fabric graft within the vessel. The Dacron® graft is compressed within the catheter and then deployed within the vessel to be treated.

A similar procedure is described by Mirich et al. in "Percutaneously Placed Endovascular Grafts for Aortic Aneurysms: Feasibility Study," *Radiology* (1989). Mirich et al. describe therein a self-expanding metallic structure covered by a nylon fabric, the structure being anchored by barbs at the proximal and distal ends.

An improvement to percutaneously delivered grafts and stent-grafts results from the use of materials such as expanded polytetrafluoroethylene (ePTFE) for a graft body. This material, and others like it, have clinically beneficial properties. However, manufacturing a graft from ePTFE can be difficult and expensive. For example, it is difficult to bond ePTFE with conventional methods such as adhesives, etc. In addition, depending on the type of ePTFE, the material can exhibit anisotropic behavior. Grafts are generally deployed in arterial systems whose environments are dynamic and which subject the devices to significant flexing and changing fluid pressure flow. Stresses are generated that are cyclic and potentially destructive to interface points of grafts, particularly interface between soft and relatively hard or high strength materials.

What has been needed is a method and device for manufacturing intracorporeal devices used to replace, strengthen or bypass body channels or lumens of a patient from ePTFE and similar materials which is reliable, efficient and cost effective.

SUMMARY

An embodiment of the invention is directed to the formation of a joint between an connector member and a flexible material portion of an endovascular graft, or section thereof. A flap of the flexible material portion is fixed about at least a portion of the connector member such that tensile force imposed on the connector member is transferred into a shear component of force on the fixed portion of the flap. Such a configuration provides a high strength joint with a low profile or low cross sectional mass that will allow the graft to be compressed radially for flexible low profile percutaneous delivery to a body conduit of a patient. Such a joining method also provides for ease of manufacture of the graft. The connector member can be an annular connector member suitable for connection to an expandable.

Another embodiment of the invention is directed to an endovascular graft or section thereof with a flexible material portion and a transversely or circumferentially oriented member secured to the flexible material portion with a joint. The joint includes at least one flap of the flexible material folded back to form a loop portion about the transversely or circumferentially oriented member. The flap is secured in the looped configuration. The flap for this embodiment and other embodiments discussed herein can be secured in the loop configuration by a variety of methods including adhesive bonding and thermomechanical compaction or seam formation. Thermomechanical compaction which can include seam formation is particularly useful when fusible material is used for the flexible material portion. The transversely or circumferentially oriented member may be a connector member, expandable stent, a portion of either of these or the like.

An embodiment of a method for securing a transversely or circumferentially oriented member to a flexible material portion of an endovascular graft or section thereof is now described. A transversely or circumferentially oriented member is disposed in proximity to a flap in the flexible material portion of the endovascular graft, or section thereof. The flap is then folded over at least a portion of the transversely or circumferentially oriented member to form a loop portion of the flap about the transversely oriented member. The flap is then secured in a looped configuration. The transversely or circumferentially oriented member may be an expandable stent, a connector member configured to be secured to an expandable stent or other component of a stent graft device.

BRIEF DESCRIPTION OF THE DRAWINGS

FIG. 25A is a transverse cross sectional view of a portion of the endovascular graft of FIG. 24 taken along lines 25A-25A of FIG. 24 which illustrates an embodiment of a joint between a transversely oriented member and flexible material portion of the endovascular graft.

FIG. 25B is a perspective view of the joint of FIG. 25A.

FIG. 26 is a transverse cross sectional view of a portion of an endovascular graft which illustrates an embodiment of a joint between a transversely oriented member and flexible material portion of the endovascular graft.

FIG. 27 is a transverse cross sectional view of a portion of an endovascular graft which illustrates an embodiment of a joint between a transversely oriented member and flexible material portion of the endovascular graft.

DETAILED DESCRIPTION

Figure 1:
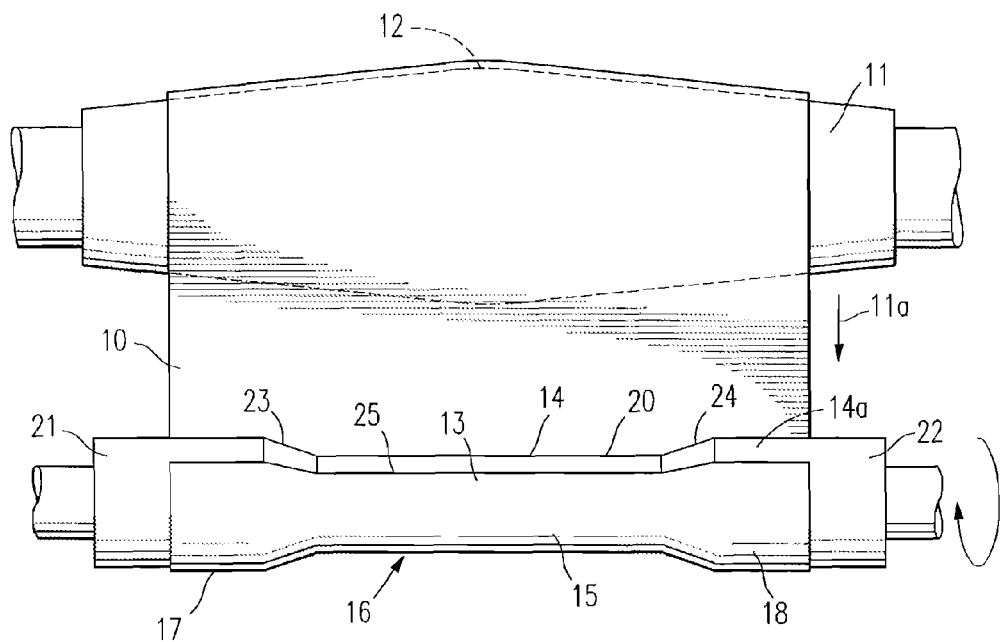
FIG. 1 illustrates a layer of fusible material being positioned onto a shape forming mandrel.

FIG. 1 illustrates a sheet of fusible material 10 stored on an elongate drum 11. The drum 11 is rotatable, substantially circular in transverse cross section and has a transverse dimension in the longitudinal center 12 that is greater than the transverse dimension of either end of the drum. The sheet of fusible material 10 is being rolled from the elongate drum in a single layer 13 onto an interior surface support means in the form of a cylindrical or tapered (conical) shape forming member or mandrel 14 to form a body section 15 of an endovascular graft 16. The body section 15 has a proximal end 17 and a distal end 18. For the purposes of this application, with reference to endovascular graft devices, the proximal end 17 describes the end of the graft that will be oriented towards the oncoming flow of bodily fluid, usually blood, when the device is deployed within a conduit of a patient's body. The distal end 18 of the graft is the end opposite the proximal end.

A single layer of fusible material 13 is a term that generally refers to a sheet of material that is not easily separated by mechanical manipulation into additional layers. The shape forming mandrel 14 is substantially cylindrical in configuration, although other configurations are possible. Middle section 20 of mandrel 14 shown in FIGS. 1-2 has a transverse dimension which is smaller than the transverse dimension of a first end section 21 and a second end section 22. The shape forming mandrel may have a first tapered section 23 at the first end and a second tapered section 24 at the second end. The sheet of fusible material 10 is shown being rolled off the elongate drum 11 in the direction indicated by the arrow 11A with the lead end 25 of the first layer of fusible material 10 oriented longitudinally along an outside surface 14A of the shape forming mandrel 14.

The fusible material in the embodiment illustrated in FIG. 1 is ePTFE that ranges from about 0.0005 to about 0.010 inch in thickness; specifically from about 0.001 to about 0.003 inch in thickness. The sheet being disposed or rolled onto the shape forming mandrel 14 may range from about 2 to about 10 inches in width; specifically, from about 3 to about 7 inches in width, depending on the indication and size of the end product.

The ePTFE material sheet 10 in FIG. 1 is a fluoropolymer with a node and fibril composition with the fibrils oriented in primarily a uniaxial direction substantially aligned with the longitudinal axis of shape forming mandrel 14. Other nodal/fibril orientations of ePTFE could also be used for this layer, including multiaxially oriented fibril configurations or uniaxial material oriented substantially circumferentially about shape forming mandrel 14 or at any desired angle between substantial alignment with the longitudinal axis and substantial alignment with a circumferential line about the shape forming mandrel 14. Uniaxially oriented ePTFE materials tend to have greater tensile strength along the direction of fibril orientation, so fibril orientation can be chosen to accommodate the greatest stresses imposed upon the finished product for the particular layer, combination of layers, and portion of the product where such stress accommodation is needed.

The layers of fusible material made of ePTFE are generally applied or wrapped in an unsintered state. By applying the ePTFE layers in an unsintered or partially sintered state, the graft body section 15, upon completion, can then be sintered or fixed as a whole in order to form a cohesive monolithic structure with all contacting surfaces of ePTFE layers achieving some level of interlayer adhesion. It may, however, be desirable to apply some layers of fusible material that have been pre-sintered or pre-fixed in order to achieve a desired result or to assist in the handling of the materials during the construction process. For example, it may be desirable in some embodiments to sinter the single layer 13 of fusible material applied to the shape forming mandrel 14 in order to act as a better insulator between the shape forming mandrel 14, which can act as a significant heat sink, and subsequent layers of fusible material which may be welded by seam formation in some locations in order to create inflatable channels.

The amount of expansion of the ePTFE material used for the construction of endovascular grafts and other devices can vary significantly depending on the desired characteristics of the material and the finished product. Typically, the ePTFE materials processed by the devices and methods discussed herein may have a density ranging from about 0.4 to about 2 grams/cc; specifically, from about 0.5 to about 0.9 grams/cc. The nodal spacing of the uniaxial ePTFE material may range from about 0.5 to about 200 microns; specifically, from about 5 to about 35 microns. The nodal spacing for multiaxial ePTFE material may range from about 0.5 to about 20 microns; specifically, from about 1 to about 2 microns.

Although FIG. 1 illustrates a layer of fusible material that is made of ePTFE, the methods described herein are also suitable for a variety of other fusible materials. Examples of other suitable fusible materials for endovascular graft construction and other applications include PTFE, porous PTFE, ultra high molecular weight polyethylene, polyesters, and the like.

Figure 2:
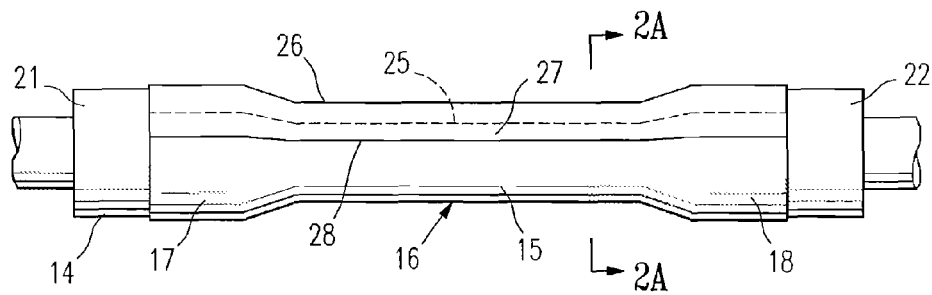
FIG. 2 shows a first layer of fusible material disposed on a shape forming mandrel.
Figure 2A:
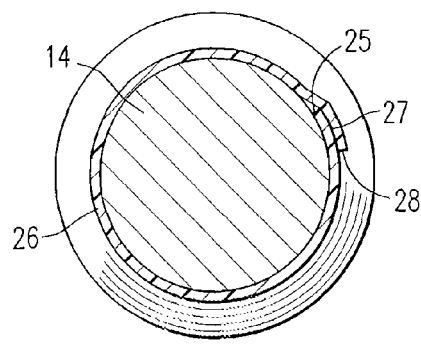
FIG. 2A is a transverse cross sectional view of the first layer of fusible material and the shape forming mandrel of FIG. 2 taken along lines 2A-2A in FIG. 2.

FIGS. 2 and 2A depict a first layer of fusible material 26 disposed on the shape forming mandrel 14 with an overlapped portion 27 of the first layer 26 on itself. A terminal end 28 of the first layer 26 is seen extending longitudinally along the length of the shape forming mandrel 14. As the layer of fusible material is wrapped onto shape forming mandrel 14, some tension may be provided on the sheet of material by the elongate drum 11. As a result of this tension and the flexible and conforming properties of the ePTFE material, the first layer of material 26 conforms closely to the outer contour of the shape forming mandrel 14 as is illustrated in FIG. 2.

In some embodiments, it may be desirable to pass the tip of a seam forming tool or similar device (not shown) along the overlapped portion 27 of first layer 26 in a longitudinal direction in order to form a seam (not shown) along the overlapped portion 27 of first layer 26. A tool suitable for forming such a longitudinal seam is a soldering iron with a smooth, rounded tip that will not catch or tear the layer of fusible material. An appropriate operating temperature for the tip of such a tool may range from about 320 to about 550 degrees Celsius; specifically, from about 380 to about 420 degrees Celsius.

Figure 3:
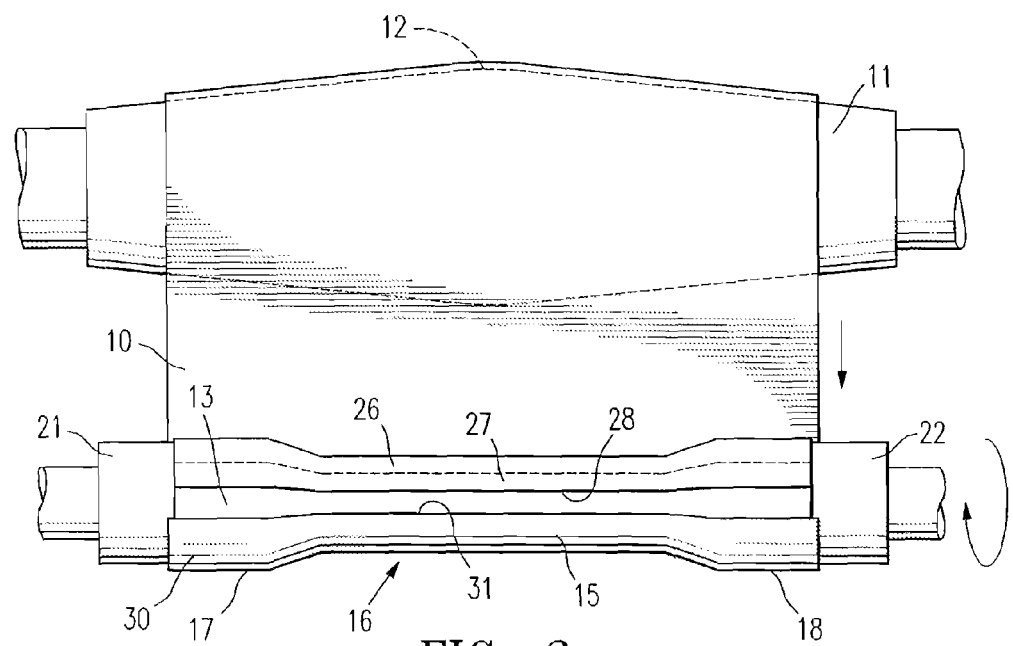
FIG. 3 illustrates an additional layer of fusible material being deposited onto a shape forming mandrel.

FIG. 3 illustrates an additional layer of fusible material 30 being disposed or wrapped onto the first layer of fusible material 26 in a manner similar to that described above for the first layer 26. Both uniaxial and multiaxial ePTFE may be used for this additional layer 30. A lead end 31 of the additional layer can be seen adjacent the terminal end 28 of the first layer 26. Tension on the additional layer of fusible material 30 helps to make the additional layer 30 conform to the shape forming mandrel 14 as seen in the illustration. Although a single additional layer 30 is shown in FIG. 3 as being disposed onto the first layer 26, it is within the scope of the invention to wrap multiple additional layers 30 of fusible material in this step. We have found that wrapping two additional layers 30 of multiaxial ePTFE onto the first layer 26 helps to form a useful graft body section 15.

Figure 4:
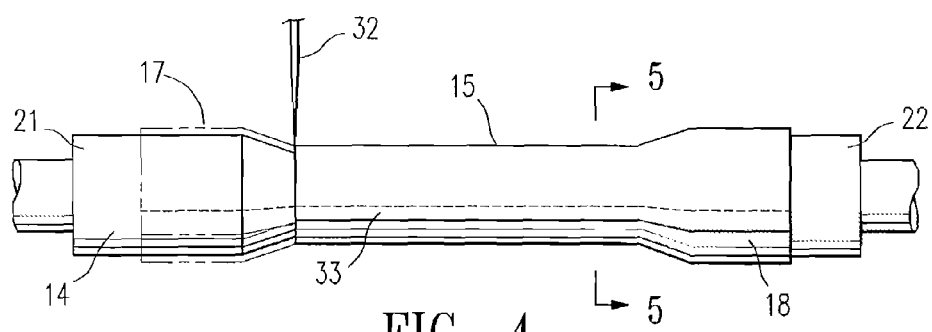
FIG. 4 shows the first layer of fusible material being trimmed by an instrument.
Figure 5:
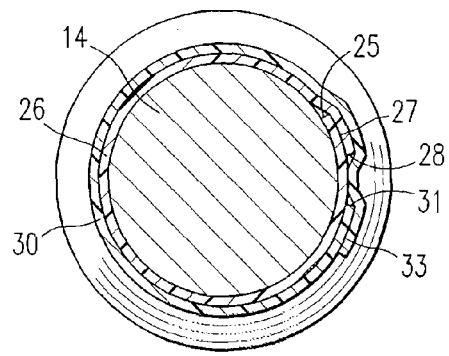
FIG. 5 is a transverse cross sectional view of the layers of fusible material and shape forming mandrel of FIG. 5 taken along lines 5-5 of FIG. 4.

FIG. 4 shows an optional step in which the first and additional layers of fusible material 26 and 30 which form the graft body section 15 under construction are trimmed by knife edge 32 or a similar tool which is pressed against the layers of material and moved circumferentially about the shape forming mandrel 14. FIG. 5 is a transverse cross sectional view of the shape forming mandrel 14 and graft body section 15 of FIG. 5 taken along lines 5-5 in FIG. 4. The overlapped portion 27 of the first layer 26 and an overlapped portion 33 of the additional layer 30 of fusible material can be seen. It may be desirable to create a longitudinal seam in the overlapped portion 33 of the additional layer 30 in a manner similar to that of the first layer 26 discussed above using the same or similar tools.

Figure 6:
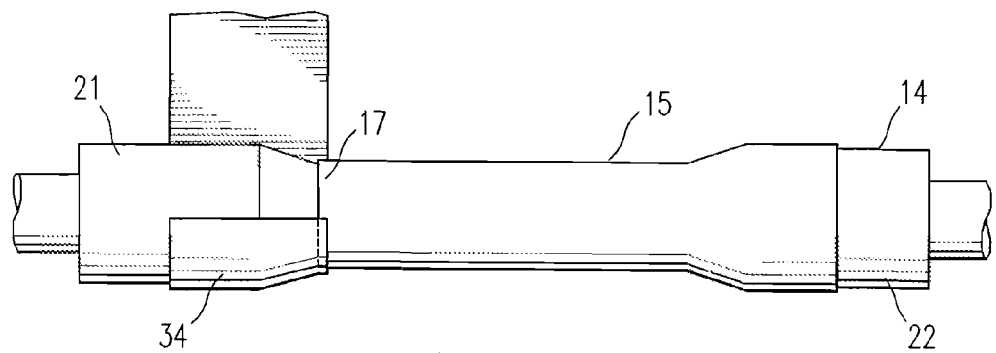
FIG. 6 illustrates additional layers of fusible material being deposited on the shape forming mandrel.

FIG. 6 illustrates a proximal end wrap 34 of fusible material being applied to the additional layer 30 of graft body section 15, preferably under some tension. We have found it useful to have end wrap 34 be uniaxial ePTFE, with the fibrils of the end wrap material oriented circumferentially about the shape forming mandrel 14, although other orientations and types of ePTFE are possible. The end wrap material may have a thickness ranging from about 0.0005 to about 0.005 inch; specifically, from about 0.001 to about 0.002 inch. The width of the end wrap material may range from about 0.25 to about 2.0 inch; specifically, from about 0.5 to about 1.0 inch. One or more layers of end wrap 34 (in any desired orientation) may be built up onto the proximal end 17 of graft body section 15 on shape forming mandrel 14. The additional end wrap layer or layers 34 may be applied in a manner similar to that of the first layer 26 and additional layers 30 as discussed above.

Figure 7:
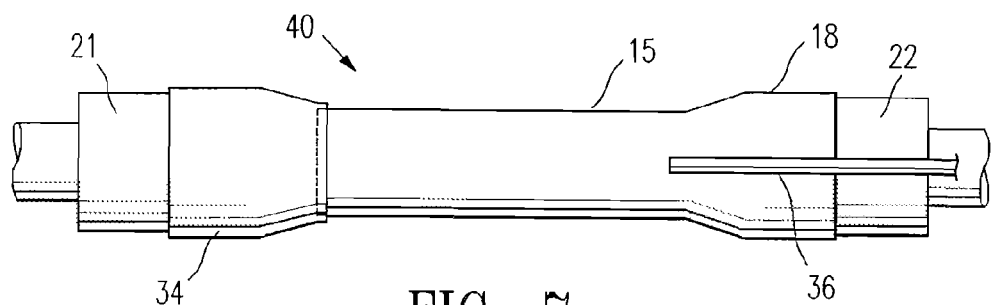
FIG. 7 illustrates an inflation line being positioned on the first and additional layers of fusible material of FIG. 6.
Figure 7A:
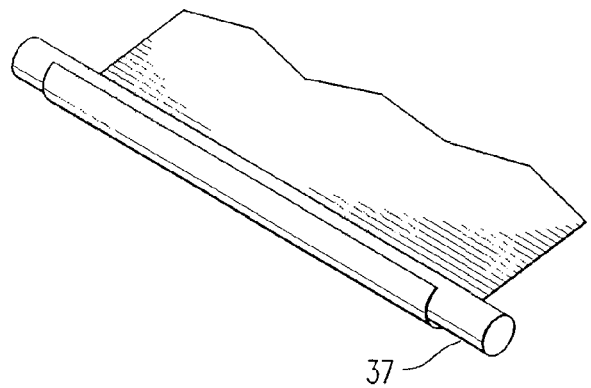
FIGS. 7A and 7B illustrate the formation of the inflation line of FIG. 7.
Figure 7B:
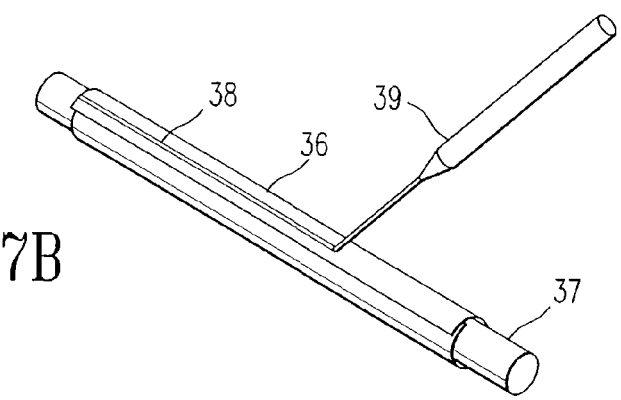

FIG. 7 shows graft body section 15 with the end wrap layer 34 completed with an inflation line 36 disposed on or near the distal end 18 of graft body section 15. The inflation line 36 may be constructed as shown in FIGS. 7A and 7B of ePTFE by wrapping one or more layers of the material about a cylindrical mandrel 37. A longitudinal seam 38 can then be formed in an overlapped portion of the layers by passing the tip of a seam forming tool 39 along the overlapped portion of the first layer in a longitudinal direction in order to form a seam 38 along the overlapped portion of the layers of the inflation line 36. A tool suitable for forming such a longitudinal seam is a soldering iron with a smooth rounded tip that will not catch or tear the layer of fusible material; operating temperatures for the tip may range as previously discussed. Alternatively, the inflation line 36 may be formed using an ePTFE extrusion placed over a mandrel.

Once seam 38 is formed in inflation line 36, the fusible material of inflation line 36 may can be fixed or sintered by heating to a predetermined temperature for a predetermined time. For embodiments of the inflation line 36 made of ePTFE, the layers are sintered by bringing the layered assembly to a temperature ranging from about 335 to about 380 degrees Celsius (for unsintered material) and about 320 to about 380 degrees Celsius (for sintering material that was previously sintered) and then cooling the assembly to a temperature ranging from about 180 to about 220 degrees Celsius. The inflation line 36 may then be removed from mandrel 37 and disposed on a graft body assembly 40 as shown in FIG. 7. The inflation line 36 may be pre-fixed or pre-sintered to avoid having the inner surfaces of the inflation line 36 stick together during the construction and processing of the graft and possibly block the inflation line 36.

Figure 8:
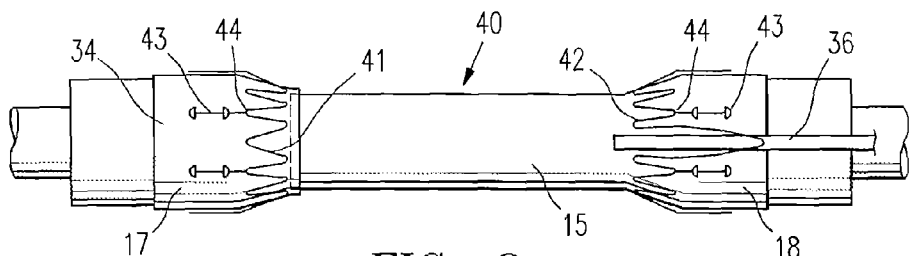
FIG. 8 shows two expandable members positioned on the layers of fusible material of FIG. 7.

In FIG. 8, expandable members in the form of a proximal connector member 41 and a distal connector member 42 have been disposed onto the graft body section 15 towards the respective graft body section proximal end 17 and distal end 18. The proximal connector member 41 is an elongate flexible metal element configured as a ring, with the ring having a zig-zag or serpentine pattern around the circumference of the ring. The distal connector member 42 can have a similar configuration; note the feature of this element in which an extended apex 44 is disposed over inflation line 36 to further stabilize graft section 15. This configuration allows the connector members 41 and 42 to be radially constrained and radially expanded while maintaining a circular ring configuration. The embodiment of the connector members 41 and 42 shown in FIG. 8 may be constructed of any suitable biocompatible material; most suitable are metals, alloys, polymers and their composites known to have superelastic properties that allow for high levels of strain without plastic deformation, such as nickel titanium (NiTi). Other alloys such as stainless steel may also be used. Connector members 41 and 42 shown are also configured to be self-expanding from a radially constrained state. The serpentine pattern of the connector members 41 and 42 is disposed over base layers of the graft body section as are connector elements 43 which are disposed on certain apices 44 of the serpentine pattern of the connector members 41 and 42. The embodiments of the connector members 41 and 42 shown in FIG. 8 have been shape formed to lie substantially flat against the contour of the outer surface of the shape forming mandrel 14. Although the embodiment of FIG. 8 illustrates connector members 41 and 42 being disposed upon the graft body section 15, expandable members including stents or the like may be used in place of the connector members 41 and 42.

Figure 9:
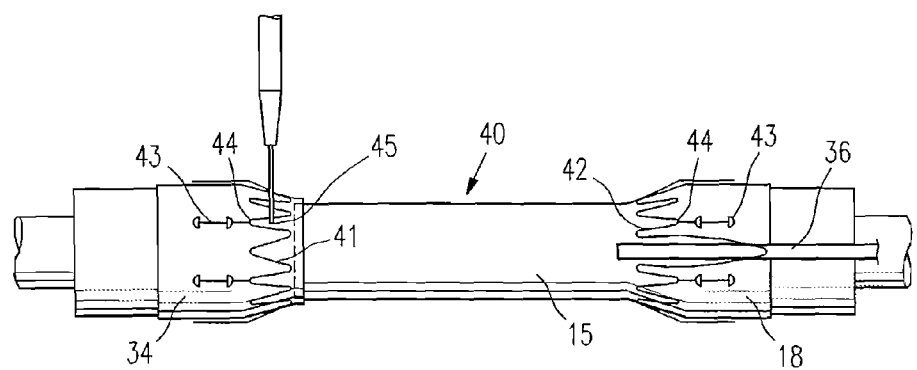
FIG. 9 illustrates the deposition of an adhesive or melt processible material adjacent a connector member of the graft body section under construction.

An optional adhesive or melt-processible material such as FEP or PFA may be deposited adjacent the connector members 41 and 42 prior to the addition of additional layers of fusible material to the graft body section 15, as is shown in FIG. 9. Materials such as FEP or PFA can help the layers of fusible material to adhere to the connector members 41 and 42, to inflation line 36 (in the case of distal member 42), and to each other. In addition, such material may serve to provide strain relief between connector members 41 and 42 and the adhered or bonded layers of fusible material (and inflation line 36) adjacent the wire of the connector members 41 and 42. It has been determined that one of the areas of greatest concentrated stress within an endovascular structure such as that described herein, when deployed within a dynamic biological system, such as an artery of a human patient, is at the junction between the connector members 41 and 42 and graft body section 15. Therefore, it may be desirable to include materials such as FEP or PFA or some other form of strength enhancement or strain relief in the vicinity of this junction.

Figure 10:
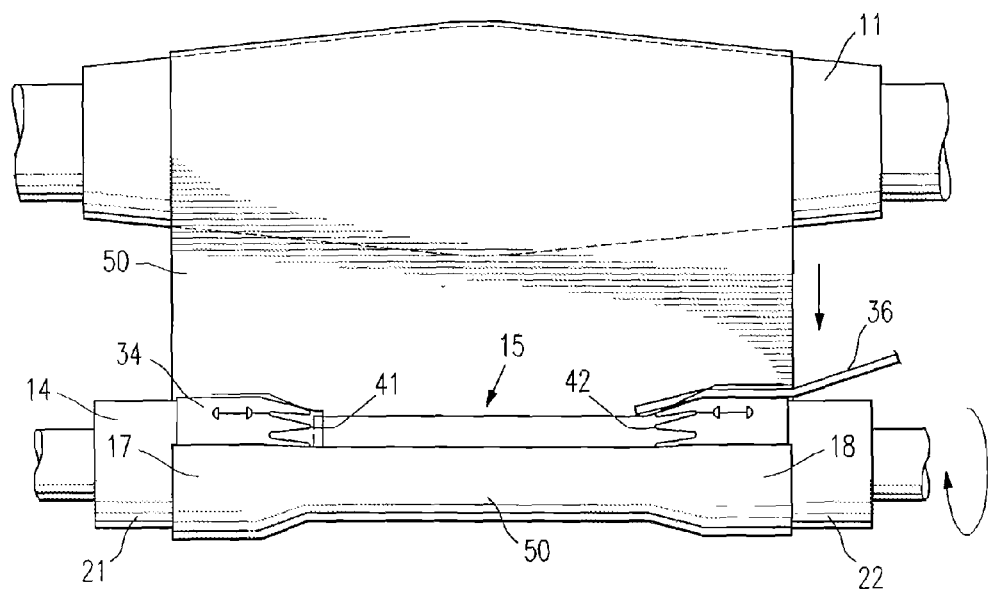
FIG. 10 shows another additional layer of fusible material being deposited onto the graft body section.

An outer overall wrap layer 50 may thereafter be applied to the graft body section 15 and connector members 41 and 42 as shown in FIG. 10. The outer overall wrap layer 50 can include one, two, three or more layers of multiaxial ePTFE, usually about 2 to about 4 layers, but uniaxial ePTFE other suitable fusible materials, fibril orientation and layer numbers could also be used. The outer overall wrap layer 50 is most usefully applied under some tension in order for the layer or layers to best conform to the outer contour of the shape forming mandrel 14 and graft body section 15. When the outer layer 50 comprises multiaxial ePTFE, there is generally no substantially preferred orientation of nodes and fibrils within the microstructure of the material. This result in a generally isotropic material whose mechanical properties, such as tensile strength, are generally comparable in all directions (as opposed to significantly different properties in different directions for uniaxially expanded ePTFE). The density and thickness of the multiaxial material can be the same as or similar to those dimensions discussed above.

Although not shown in the figures, we have found it useful to add one or more optional cuff-reinforcing layers prior to the addition of an overall wrap layer 50 as discussed below in conjunction with FIG. 10. Typically this cuff-reinforcing layer is circumferentially applied to graft body section 15 at or near the graft body section proximal end 17 so to provide additional strength to the graft body section proximal end 17 in those designs in which a proximal cuff (and possibly a proximal rib) are used. Typically the graft experiences larger strains during fabrication and in service in the region of the proximal cuff, especially if a larger cuff is present. This optional cuff-reinforcing layer typically is multiaxial ePTFE, although uniaxial ePTFE and other materials may be used as well. We have found effective a cuff-reinforcing layer width from about 20 to about 100 mm; specifically, about 70 mm. Functionally, however, any width sufficient to reinforce the proximal end of graft body section 15 may be used.

Figure 11:
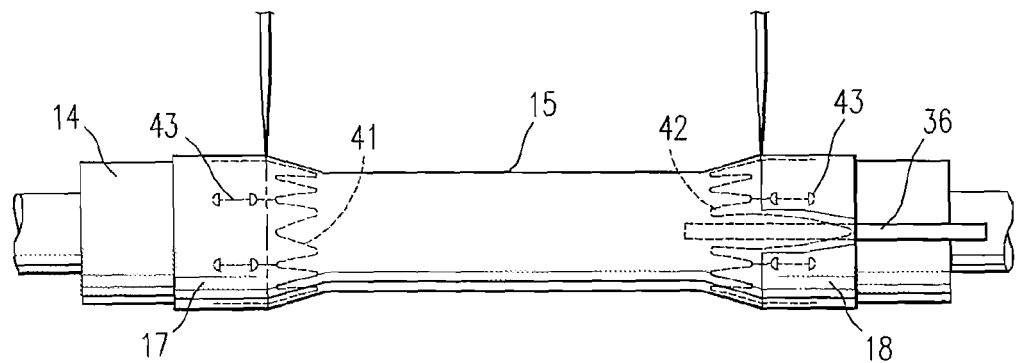
FIG. 11 illustrates excess fusible material being trimmed from the first end and second end of the graft body section adjacent the connector members.
Figure 12:
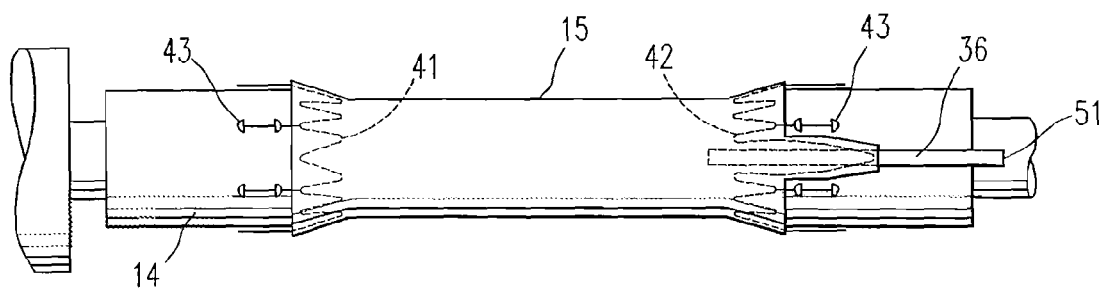
FIG. 12 is an elevational view of the graft body section with the fusible material trimmed away and removed.

Once the additional layer or layers of fusible material and additional graft elements such as the connector members 41 and 42 and inflation line 36 have been applied, any excess fusible material may be trimmed away from the proximal end 17 and distal end 18 of graft body section 15. FIG. 11 illustrates one or more layers of fusible material being trimmed from the proximal end 17 and distal end 18 of the graft body section 15 so as to leave the connector members 41 and 42 embedded between layers of fusible material but with the connector elements 43 exposed and a distal end 51 of the inflation line 36 exposed as shown in FIG. 12. Once the fusible material has been trimmed from the proximal end 17 and the distal end 18, as discussed above, an additional process may optionally be performed on the proximal end 17, distal end 18 or both the proximal end and distal end 17 and 18. In this optional process (not shown in the figures), the outer wrap 50 is removed from a portion of the connector members 41 and 42 so as to expose a portion of the connector members 41 and 42 and the additional layer of fusible material 30 beneath the connector member 42 and the proximal end wrap 34 beneath connector member 41. Once exposed, one or more layers of the additional layer or layers 30 or proximal end wrap 34 may have cuts made therein to form flaps which can be folded back over the respective connector members 42 and 41 and secured to form a joint (not shown). One or more layers of fusible material can then be disposed over such a joint to provide additional strength and cover up the joint.

Once the graft body section 15 has been trimmed, the entire shape forming mandrel 14 and graft body section 15 assembly is moved to a seam forming apparatus 52 illustrated in FIGS. 13A-13H. This seam forming apparatus 52 has a base 53 and a vertical support platform 54 which extends vertically upward from the back edge of the base 53. A mount system 55 is secured to the base 53 and for the embodiment shown in the figures, consists of a motor drive chuck unit 56 secured to a riser 57 and a live center unit 58 secured to a riser 59. Both risers 57 and 59 are secured to the base 53 as shown. The axis of rotation 55A of the chuck 60 of the motor drive chuck unit 56 and the axis of rotation 55B of the live center 61 of the live center unit 58 are aligned or concentric as indicated by dashed line 55C. A motor is mechanically coupled to the chuck 60 of the motor drive chuck unit 56 and serves to rotate the chuck 60 in a controllable manner.

A vertical translation rack 62 is secured to the vertical support platform 54 and extends from the base 53 to the top of the vertical support platform 54. A vertical car 63 is slidingly engaged on the vertical translation rack 62 and can be moved along the vertical translation rack 62, as shown by arrows 63A, in a controllable manner by a motor and pinion assembly (not shown) secured to the vertical car 63. A horizontal translation rack 64 is secured to the vertical car 63 and extends from the left side of the vertical car 63 to the right side of the vertical car 63. A horizontal car 65 is slidingly engaged on the horizontal translation rack 64 and can be moved along the horizontal rack 64, as shown by arrow 64A, in a controllable manner by a motor and pinion assembly (not shown) which is secured to the horizontal car 65.

A stylus rotation unit 66 is slidingly engaged with a second horizontal translation rack 65A disposed on the horizontal car 65 and can be moved towards and away from the vertical car 63 and vertical support platform 54 in a controllable manner as shown by arrow 66A. A stylus rotation shaft 67 extends vertically downward from the stylus rotation unit 66 and rotates about an axis as indicated by dashed line 67B and arrow 67A in a controllable manner. A stylus mount 68 is secured to the bottom end of the rotation shaft 67 and has a main body portion 69 and a stylus pivot shaft 70. A stylus housing 71 is rotatably secured to the stylus mount 68 by the stylus pivot shaft 70. A torsion spring 72 is disposed between the proximal end of the stylus housing 73 and the stylus mount 68 and applies a predetermined amount of compressive, or spring-loaded force to the proximal end 73 of the stylus housing 71. This in turn determines the amount of tip pressure applied by a distal extremity 80 of a stylus tip 75 disposed at the distal end section 78 of the stylus 79 (which is in turn secured to the distal end section 76 of the stylus housing 71).

The base 53 of seam forming apparatus 52 is secured to a control unit housing 77 which contains one or more power supplies, a CPU, and a memory storage unit that are used in an automated fashion to control movement between the graft body 15 section and the stylus tip 75 in the various degrees of freedom therebetween. The embodiment of the seam forming apparatus 52 described above has five axes of movement (or degrees of freedom) between an object secured to the chuck 60 and live center 61 and the stylus tip 75; however, it is possible to have additional axes of movement, such as six, seven, or more. Also, for some configurations and seam forming processes, it may be possible to use fewer axes of movement, such as two, three, or four. In addition, any number of configurations may be used to achieve the desired number of degrees of freedom between the stylus 79 and the mounted device. For example, additional axes of translation or rotation could be added to the mount system and taken away from the stylus rotation unit 66. Although the embodiment of the shape forming mandrel 14 shown in FIGS. 1-17 is cylindrical, a five axis or six axis seam forming apparatus has the capability and versatility to accurately create seams of most any desired configuration on a shape forming member or mandrel of a wide variety of shapes and sizes. For example, a "Y" shaped mandrel suitable for generating a bifurcated graft body section could be navigated by the five axis seam forming apparatus illustrated herein, as well as other shapes. Finally, seam forming apparatus 52 illustrated herein is but one of a number of devices and configurations capable of achieving the seams of the present inventions.

Figure 13A:
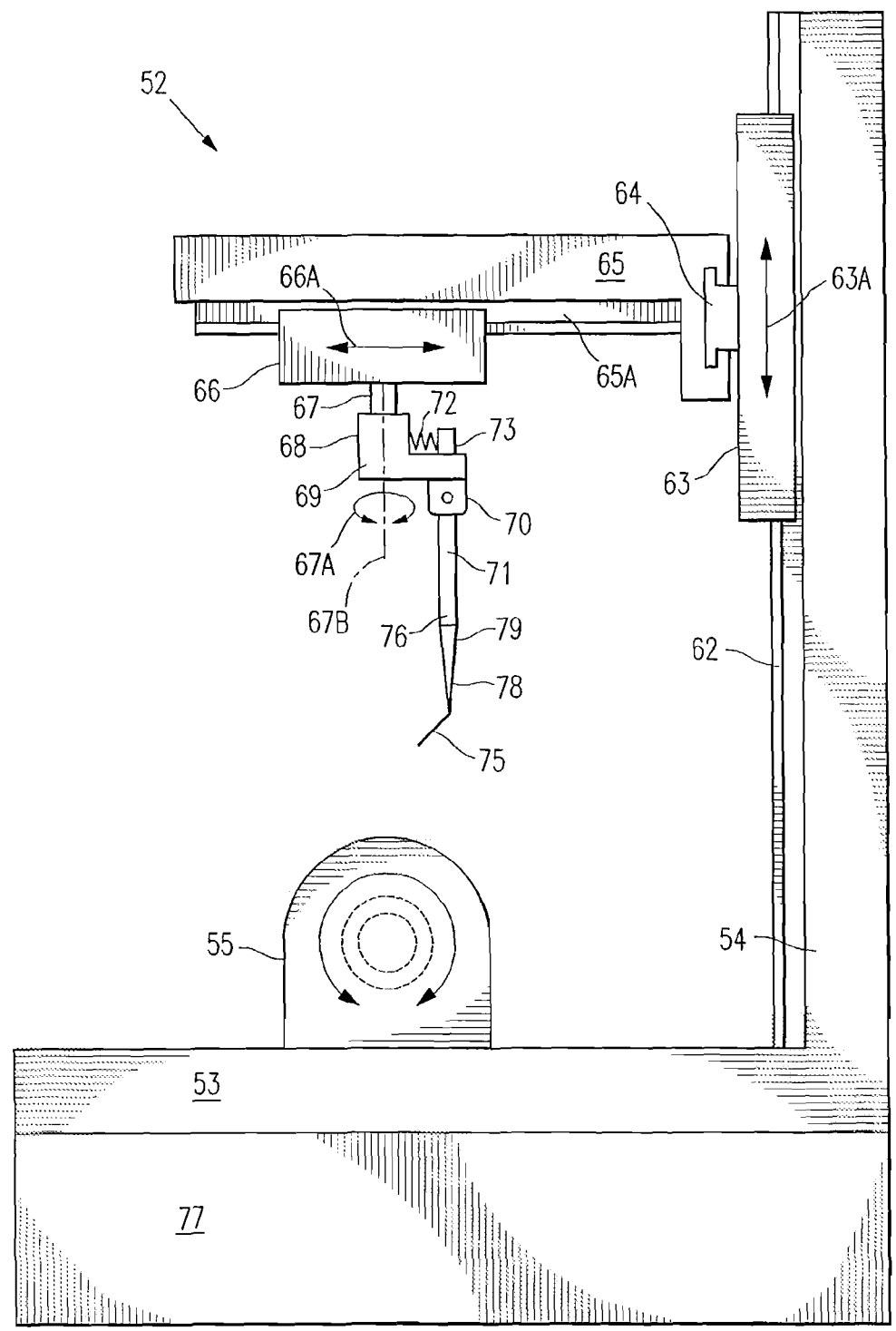
FIG. 13A is a side view from the right hand side of a five axis seam forming apparatus.
Figure 13B:
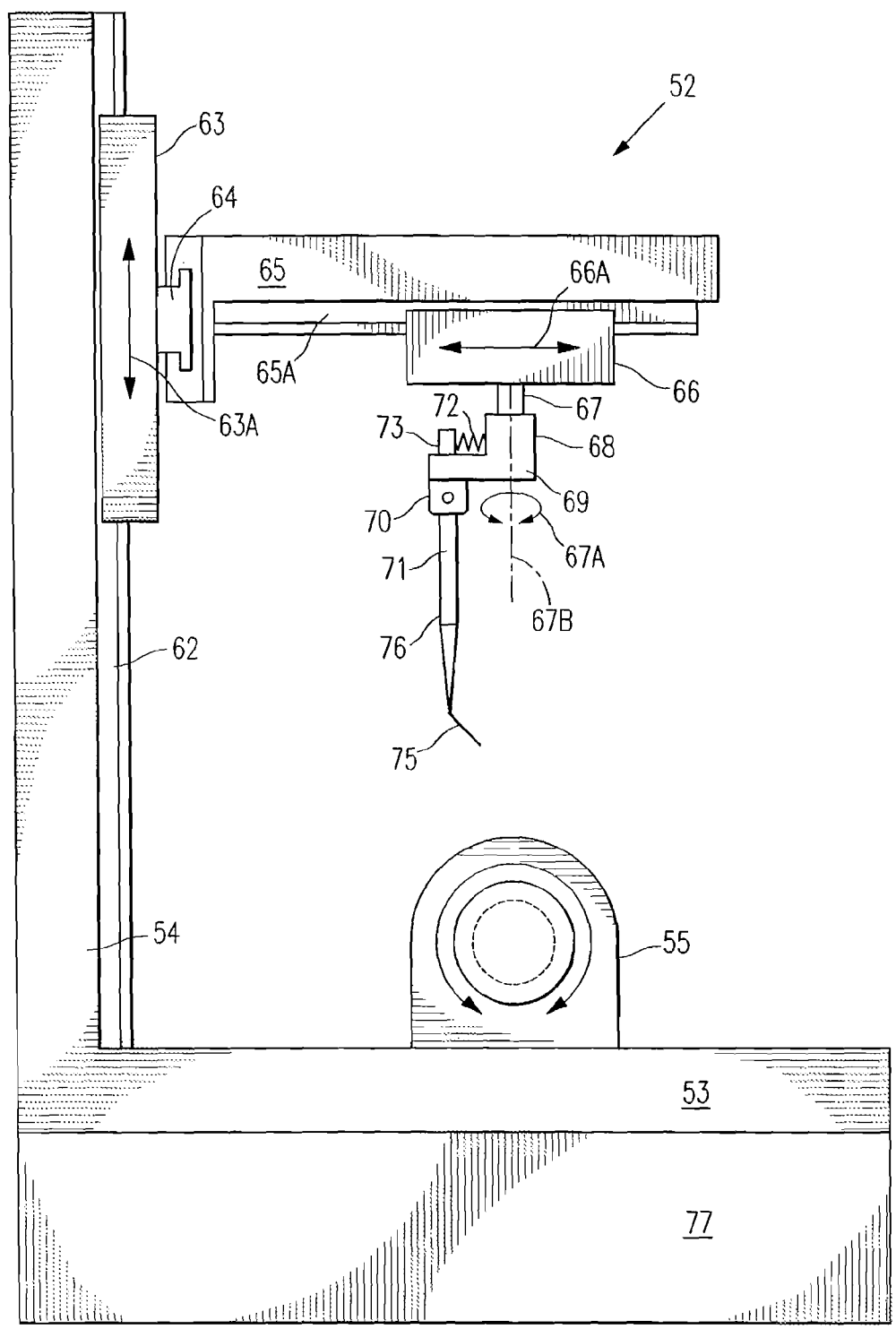
FIG. 13B is a side view from the left hand side of a five axis seam forming apparatus.
Figure 13C:
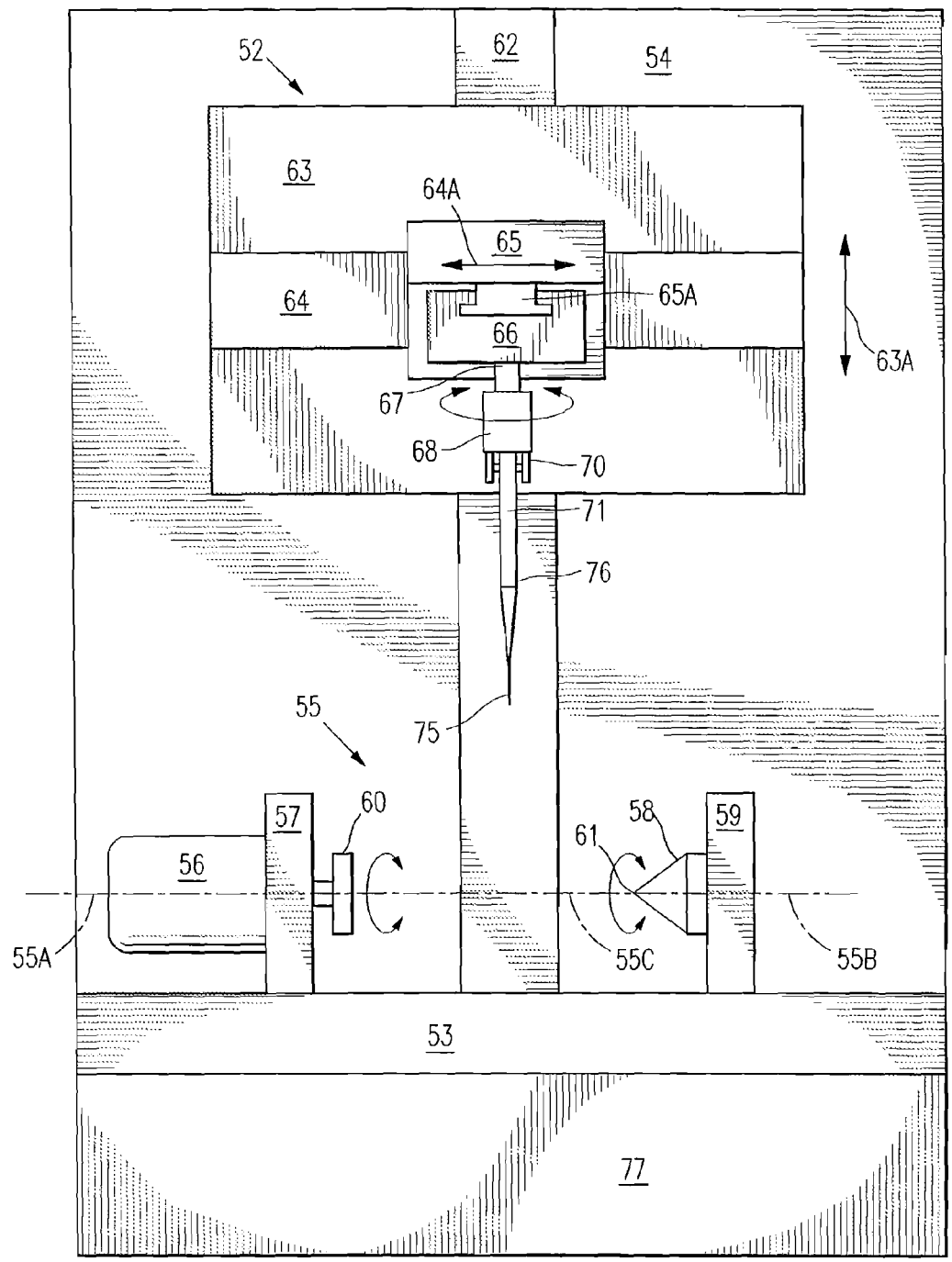
FIG. 13C is a front view of the five axis seam forming apparatus of FIGS. 13A and 13B.
Figure 13D:
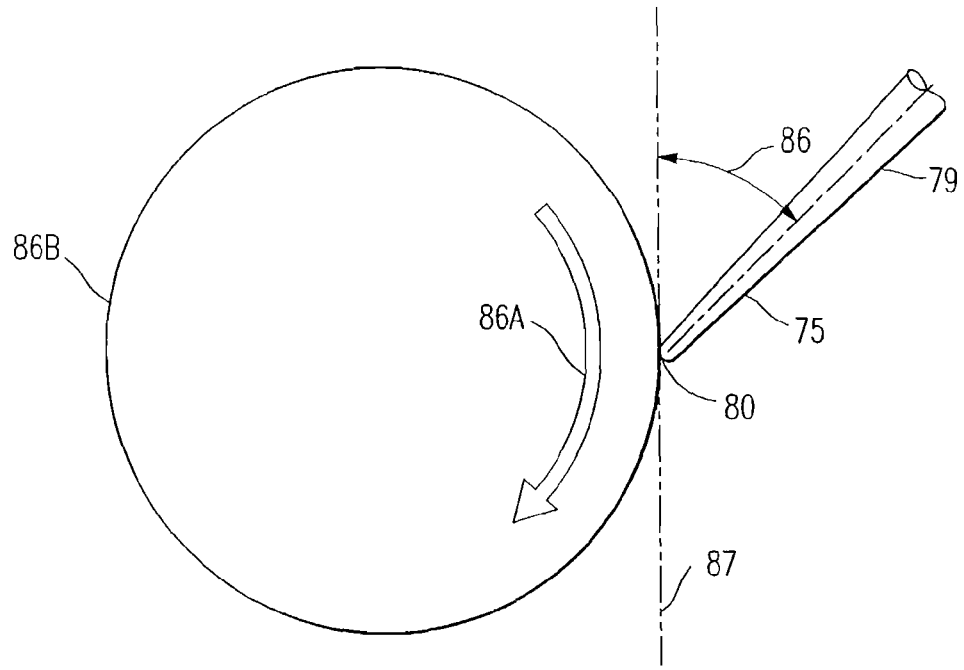
FIG. 13D shows a stylus tip in contact with a transverse cross sectioned view of a cylindrical shape forming member with an axis of the stylus tip oriented at an angle with the tangent of the shape forming member at the point of contact therebetween.

FIG. 13D illustrates an enlarged view of a stylus tip 75 applied to a rotating cylindrical surface 86B with the surface rotating in a counterclockwise direction as indicated by arrow 86A. The cylindrical surface can support one or more layers of fusible material (not shown) between the distal extremity 80 of the stylus tip 75 and the surface 86B which require seam to be formed therein. The stylus tip 75 has a longitudinal axis that forms an angle 86 with a tangent to the surface of the cylindrical surface indicated by dashed line 87. Although not necessary, we have found it useful to have the object in contact with the stylus tip 75 rotating or moving in a direction as show in FIG. 13D, relative to angle 86 in order to prevent chatter of the configuration or distortion of fusible material on the surface 86A. In one embodiment, angle 86 may range from about 5 to about 60 degrees; specifically, from about 10 to about 20 degrees. It is also useful if the distal extremity 80 of the stylus tip 75 has a smooth surface and is radiused. A suitable radius for one embodiment may range from about 0.01 to about 0.030 inch; specifically, from about 0.015 to about 0.02 inch.

Figure 13E:
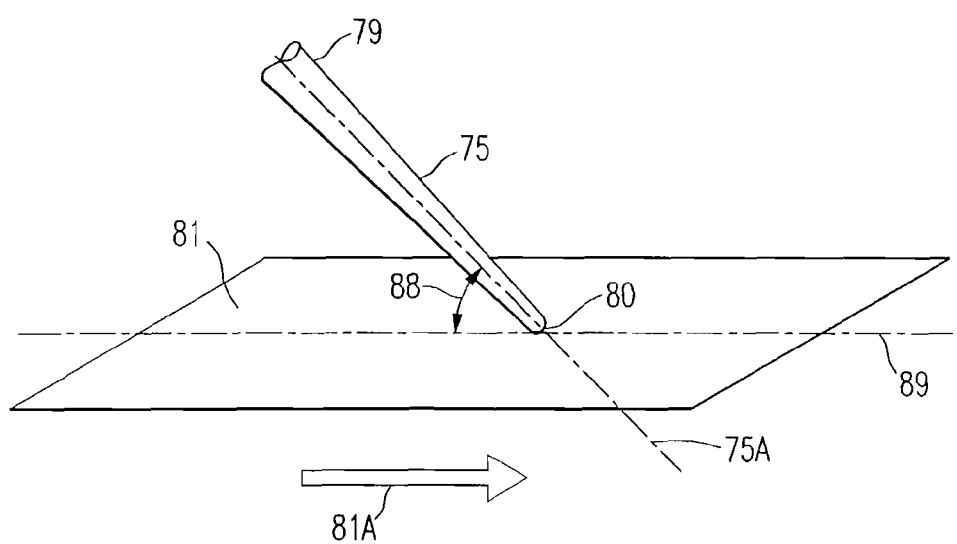
FIG. 13E illustrates a stylus tip in contact with a plurality of layers of fusible material in a substantially flat configuration with the longitudinal axis of the stylus tip at an angle with respect to a line which is orthogonal to the surface of the layers.

FIG. 13E shows a similar relationship between a stylus tip 75 and hard surface 81. Surface 81 may have one or more layers of fusible material (not shown) disposed thereon between distal extremity 80 and surface 81. A longitudinal axis 75A of stylus tip 75 forms an angle 86 with the dashed line 89 that is parallel to surface 81. Angle 88 in this embodiment should range from about 5 to about 60 degrees; specifically, from about 10 to about 20 degrees, so to ensure smooth relative motion between surface 81 and tip 75. The surface 81 is shown moving relative to the stylus tip 75 in the direction indicated by arrow 81A.

The pressure exerted by the extremity 80 of stylus tip 75 on the material being processed is another parameter that can affect the quality of a seam formed in layers of fusible material. In one embodiment in which the stylus tip is heated, the pressure exerted by the distal extremity 80 of the stylus tip 75 may range from about 100 to about 6,000 pounds per square inch (psi); specifically, from about 300 to about 3,000 psi. The speed of the heated stylus 75 relative to the material being processed, such as that of graft body section 15, may range from about 0.2 to about 10 mm per second, specifically, from about 0.5 to about 1.5 mm per second. The temperature of the distal extremity 80 of the heated stylus tip 75 in this embodiment may range from about 320 to about 550 degrees Celsius; specifically, about 380 to about 420 degrees Celsius.

Seam formation for ePTFE normally occurs by virtue of the application of both heat and pressure. The temperatures at the tip of the heated stylus 75 during such seam formation are generally above the melting point of highly crystalline ePTFE, which may range be from about 327 to about 340 degrees Celsius, depending in part on whether the material is virgin material or has previously been sintered). In one embodiment, the stylus tip temperature for ePTFE welding and seam formation is about 400 degrees Celsius. Pressing such a heated tip 75 into the layers of ePTFE against a hard surface such as the outside surface of the shape forming mandrel) compacts and heats the adjacent layers to form a seam with adhesion between at least two of, if not all, the layers. At the seam location and perhaps some distance away from the seam, the ePTFE generally transforms from an expanded state with a low specific gravity to a non-expanded state (i.e., PTFE) with a relatively high specific gravity. Some meshing and entanglement of nodes and fibrils of adjacent layers of ePTFE may occur and add to the strength of the seam formed by thermal-compaction. The overall result of a well-formed seam between two or more layers of ePTFE is adhesion that can be nearly as strong or as strong as the material adjacent the seam. The microstructure of the layers may change in the seam vicinity such that the seam will be impervious to fluid penetration.

It is important to note that a large number of parameters determine the proper conditions for creating the fusible material seam, especially when that material is ePTFE. Such parameters include, but are not limited to, the time the stylus tip 75 is in contact with the material (or for continuous seams, the rate of tip movement), the temperature (of the tip extremity 80 as well as that of the material, the underlying surface 81, and the room), tip contact pressure, the heat capacity of the material, the mandrel, and the other equipment, the characteristics of the material (e.g. the node and fibril spacing, etc.), the number of material layers present, the contact angle between the tip extremity 80 and the material, the shape of the extremity 80, etc. Knowledge of these various parameters is useful in determining the optimal combination of controllable parameters in forming the optimal seam. And although typically a combination of heat and pressure is useful in forming an ePTFE seam, under proper conditions a useful seam may be formed by pressure at ambient temperature (followed by elevation to sintering temperature); likewise, a useful seam may also be formed by elevated temperature and little-to-no applied pressure.

For example, we have created seams in ePTFE that formed an intact, inflatable cuff by the use of a clamshell mold that presented an interference fit on either side of a cuff zone for the ePTFE. The application of pressure alone without using an elevated temperature prior to sintering formed a seam sufficient to create a working cuff.

Figure 13F:
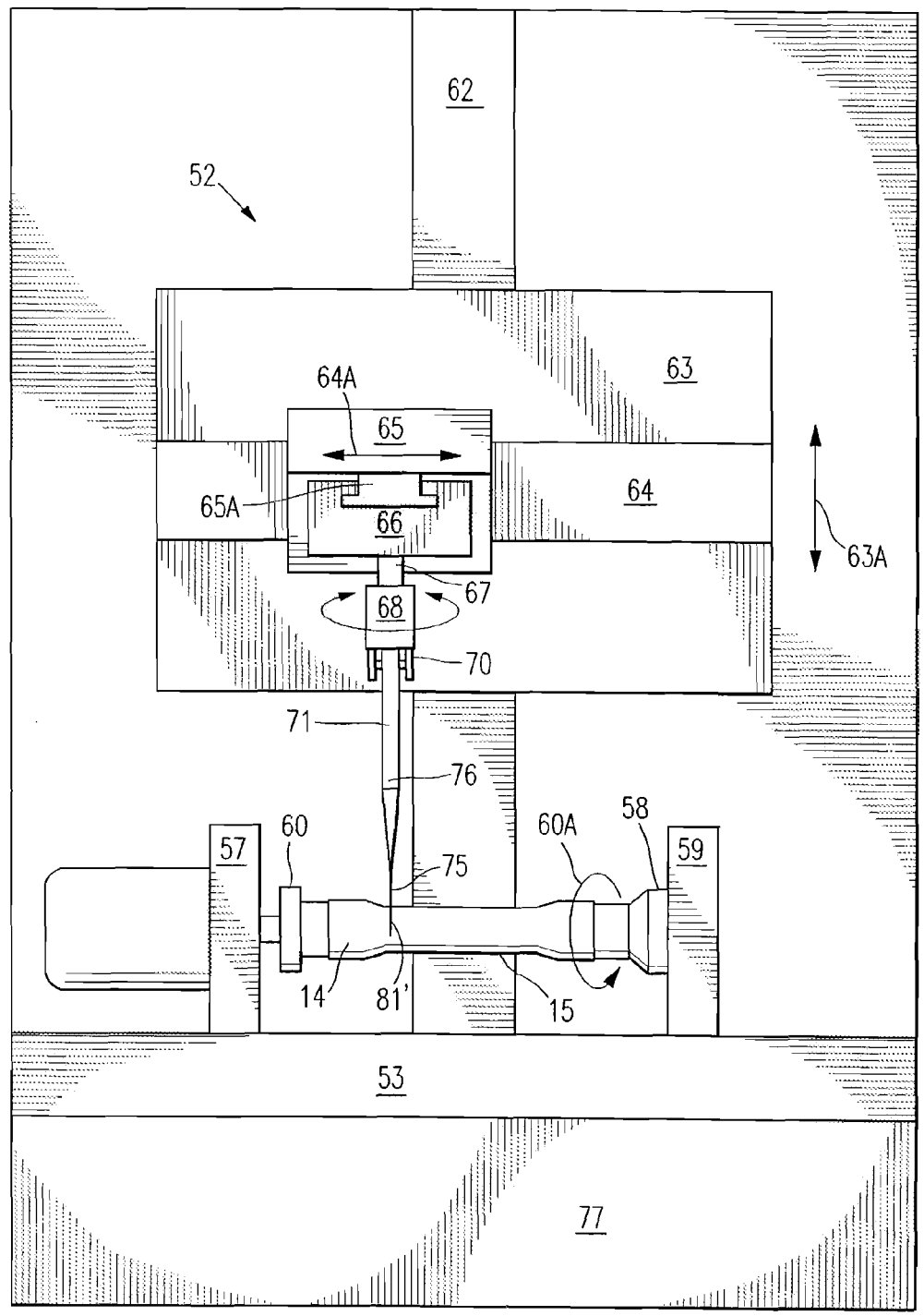
FIG. 13F is a front view of the seam forming apparatus with a shape forming mandrel and a graft body section on the shape forming mandrel positioned in the chuck of the seam forming member mount system.

FIG. 13F depicts a front view of the seam forming apparatus 52 with a shape forming mandrel 14 secured to the chuck 60 and the live center unit 58. The distal extremity of the heated stylus tip 75 is in contact with the graft body section 15 which is disposed on the shape forming mandrel 14. The chuck 60 is turning the shape forming mandrel 14 and graft body section 15 in the direction indicated by the arrow 60A to form a seam 81 between the layers of fusible material of the graft body section 15.

Figure 13G:
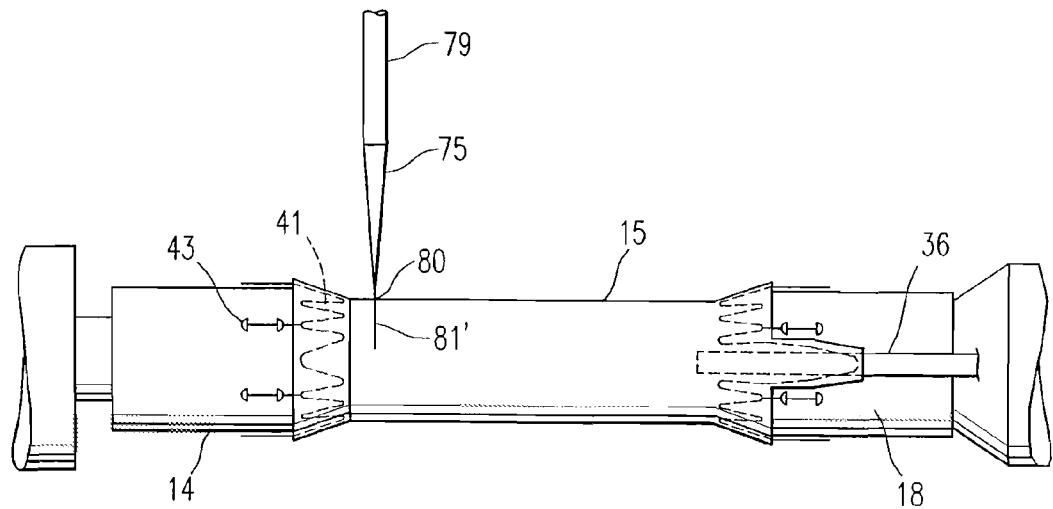
FIG. 13G illustrates a distal extremity or tip of a stylus in contact with the layers of fusible material of the graft body section.
Figure 13H:
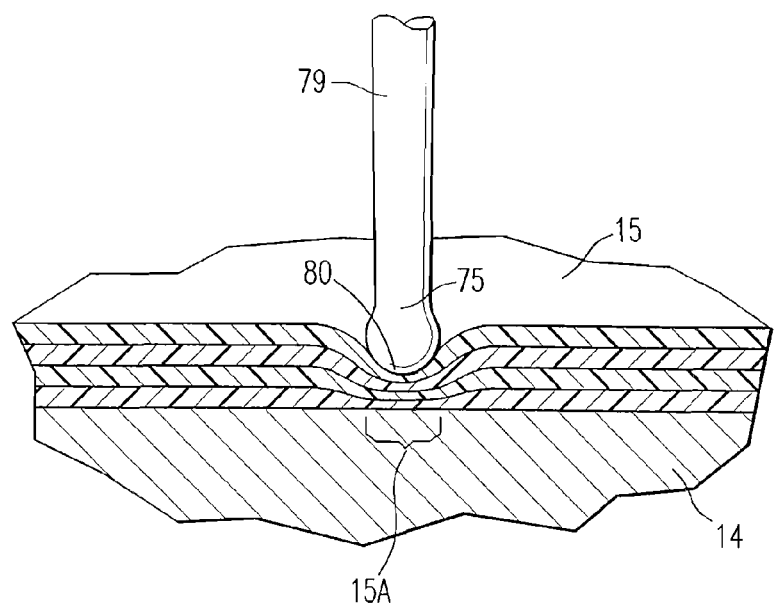
FIG. 13H illustrates the tip of a stylus in contact with layers of fusible material of the graft body section, forming a seam in the layers.

FIGS. 13G and 13H illustrate an enlarged view of the heated stylus tip 75 in contact with the graft body section 15 in the process of creating one ore more seams 81 which are configured to form elongate inflatable channels 82 in the graft body section 15. The term "inflatable channels" may generally be described herein as a substantially enclosed or enclosed volume between layers of fusible material on a graft or graft section, and in some embodiments, in fluid communication with at least one inlet port for injection of inflation material. The enclosed volume of an inflatable channel or cuff may be zero if the inflatable cuff or channel is collapsed in a non-expanded state. The enclosed volume of an inflatable channel may or may not be collapsible during compression or compacting of the graft body section 15.

FIG. 13H is an enlarged view in section of the distal extremity 80 of the heated stylus tip 75 in contact with layers of fusible material of graft body section 15. The layers of fusible material are being heated and compressed to form a bond 15A therebetween. The seam forming apparatus can position the distal extremity 80 at any desired location on the graft body section 15 by activation of one or more of the five motors controlled by the components in the control unit housing 77. Each of the five motors controls relative movement between graft body section 15 and distal extremity 80 in one degree of freedom. Thus, the distal extremity 80 may be positioned above the surface of the graft body section 15, as shown in FIG. 13C, and brought to an appropriate temperature for seam formation, as discussed above, by resistive heating or any other appropriate method. Once extremity 80 has reached the target temperature, it can be lowered by activation of the motor which controls movement of the vertical car. The extremity 80 can be lowered and horizontally positioned by other control motors until it contacts the graft body section in a desired predetermined position on graft body section 15, as shown in FIG. 13F.

Once distal extremity 80 makes contact with graft body section 15 with the proper amount of pressure, it begins to form a seam between the layers of the fusible material of the graft body section as shown in FIG. 13H. The pressure or force exerted by the extremity 80 on the graft body section may be determined by the spring constant and amount of deflection of torsion spring 72 shown in FIGS. 13A and 13B; generally, we have found a force at the extremity 80 ranging from about 0.2 to about 100 grams to be useful. As the seam formation process continues, the surface of graft body section 15 may be translated with respect to the distal extremity 80 while desirably maintaining a fixed, predetermined amount of pressure between the distal extremity 80 and the layers of fusible material of the graft body section. The CPU (or an equivalent device capable of controlling the components of apparatus 52) of the control unit housing 77 may be programmed, for instance, a mathematical representation of the outer surface contour of any known shape forming member or mandrel.

The CPU is thereby able to control movement of the five motors of apparatus 52, so that distal extremity 80 may follow the contour of the shape forming member while desirably exerting a fixed predetermined amount of pressure the layers of fusible material disposed between the distal extremity 80 and the shape forming member. While seam formation is taking place, the pressure exerted by the distal extremity 80 on the shape forming member may be adjusted dynamically. The extremity 80 may also be lifted off the graft body section and shape forming member in locations where there is a break in the desired seam pattern. Once distal extremity 80 is positioned above the location of the starting point of the next seam following the break, the extremity 80 may then be lowered to contact the layers of fusible material, reinitiating the seam formation process.

Use of the seam forming apparatus 52 as described herein is but one of a number of ways to create the desired seams in the graft body section 15 of the present invention. Any suitable process and apparatus may be used as necessary and the invention is not so limited. For instance, seams may also be formed in a graft body section 15 by the use of a fully or partially heated clamshell mold whose inner surfaces contain raised seam-forming extensions. These extensions may be configured and preferentially or generally heated so that when the mold halves are closed over a graft body section 15 disposed on a mandrel, the extensions apply heat and pressure to the graft body section directly under the extensions, thereby "branding" a seam in the graft body section in any pattern desired and in a single step, saving much time over the technique described above in conjunction with seam forming apparatus 52.

If the fusible material comprises ePTFE, it is also possible to infuse or wick an adhesive (such as FEP or PFA) or other material into the ePTFE layers such that the material flows into the fibril/node structure of the ePTFE and occupies the pores thereof. Curing or drying this adhesive material will mechanically lock the ePTFE layers together through a continuous or semi-continuous network of adhesive material now present in and between the ePTFE layers, effectively bonding the layers together.

Figure 14:
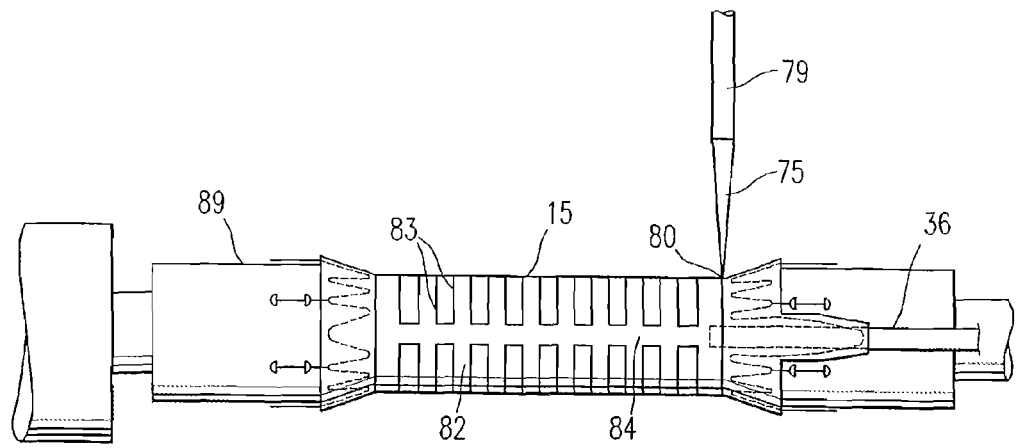
FIG. 14 shows inflation channels being formed in the layers of fusible material on the shape forming mandrel by the seam forming apparatus stylus tip.
Figure 15:
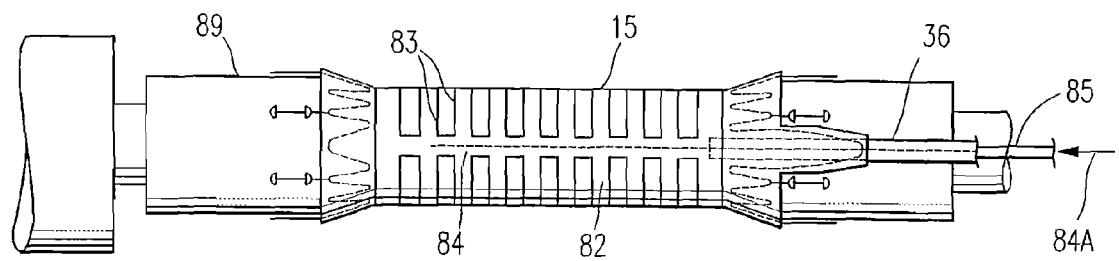
FIG. 15 shows the graft body section with the channel formation complete and pressurized fluid being injected into an inflatable channel network in order to expand the inflatable channels.

FIG. 14 illustrates a substantially completed set of seams 81 formed in the layers of fusible material of the graft body section 15, which seams form inflatable channels 82. FIG. 15 illustrates graft body section 15 as fluid (such as compressed gas) is injected into the inflation line 36 and in turn into the inflatable channel network 84 of body section 15, as shown by arrow 84A. The fluid is injected to pre-stress the inflatable channels 82 of body section 15 and expand them outward radially. The fluid may be delivered or injected through an optional elongate gas containment means having means for producing a permeability gradient in the form of a manifold or pressure line 85. The pressure line 85 shown in FIG. 15 has a configuration with an input (not shown) located outside the inflation line and a plurality of outlet apertures or orifices (not shown) that may be configured to provide an even distribution of pressure within the inflatable channel network 84. Other fluid injection schemes and configurations are of course possible.

Because ePTFE is a porous or semi-permeable material, the pressure of exerted by injected fluids such as pressurized gas tends to drop off or diminish with increasing distance away from the outlet apertures or orifices (not shown) of manifold or pressure line 85. Therefore, in some embodiments, pressure line 85 may comprise apertures or orifices (not shown) which, when disposed in graft body section 15, progressively increases in size as one moves distally along the pressure line towards the proximal end 17 graft body section 15 in order to compensate for a drop in pressure both within the inflatable channel network 84 and within the manifold or pressure line 85 itself.

Figure 16A:
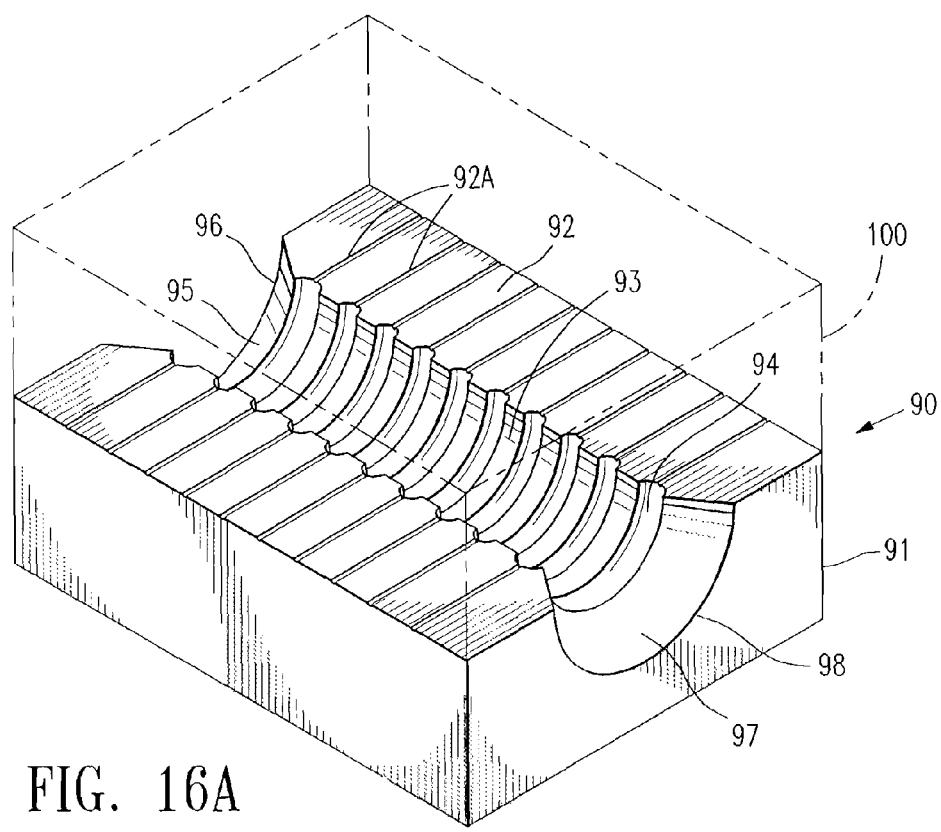
FIG. 16A illustrates one half of an embodiment of a two-piece mold for use during expansion of the inflatable channels formed by the seam forming apparatus.

Once some or all of the inflatable channels 82 have been pre-expanded or pre-stressed, the graft body section 15 and shape forming mandrel assembly 89 may then be positioned within an outer constraint means in the form of a mold to facilitate the inflatable channel expansion and sintering process. One half of a mold 90 suitable for forming an embodiment of a graft body section 15 such as that shown in FIG. 15 is illustrated in FIG. 16A. A mold half body portion 91 is one of two pieces of mold 90. A mold similar to mold 90 could be made from any number of mold body portions configured to fit together. For example, a mold 90 could be designed from three, four, five or more mold body portions configured to fit together to form a suitable main cavity portion 93 for maintaining the shape of graft body section 15 during channel expansion and sintering. For certain configurations, a one-piece mold may be used.

Mold body portion 91 has a contact surface 92 and a main cavity portion-93. Main cavity portion 93 has an inside surface contour configured to match an outside surface contour of the graft body section with the inflatable channels in an expanded state. Optional exhaust channels 92A may be formed in contact surface 92 and provide an escape flow path for pressurized gas injected into the inflatable channel network 84 during expansion of the inflatable channels 82.

Figure 16B:
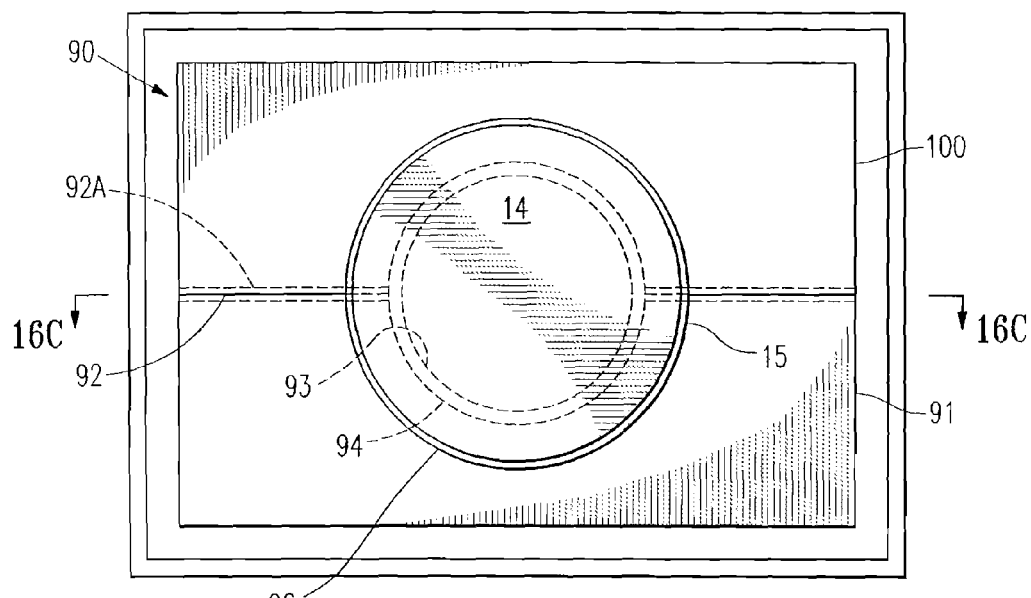
FIG. 16B is an end view showing the shape forming mandrel and graft body section within both halves of the mold.

The main cavity portion 93 of the FIGS. 16A-16B embodiment is substantially in the shape of a half cylinder with circumferential channel cavities 94 for forming the various inflatable channels 82 of graft body section 15. Cavity 93 has a first tapered portion 95 at the proximal end 96 of mold 90 and a second tapered portion 97 at the mold distal end 98. FIG. 16B shows an end view of mold 90 with the two mold body portions 91 and 100 pressed together with the assembly of the graft body section 15 and shape forming mandrel 14 disposed mold cavity 93.

Figure 16C:
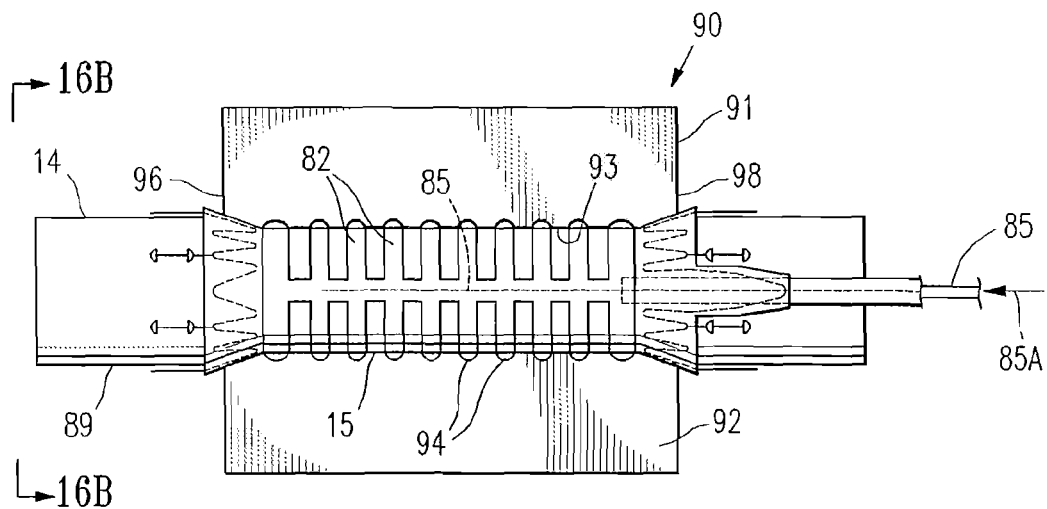
FIG. 16C shows the graft body section and shape forming mandrel disposed within the mold cavity (with one half of the mold removed for clarity of illustration) with a fluid being injected into the inflatable channels of the graft body section in order to keep the inflatable channels in an expanded state during the fixing or sintering of the fusible material.

FIG. 16C shows the assembly of the graft body section 15 and shape forming mandrel 14 disposed within mold 90, with the circumferential inflatable channels 82 of the graft body section 15 aligned with the circumferential channel cavities 94 of the main cavity portion 93. One mold body portion 100 of mold 90 is not shown for the purpose of clarity of illustration. A pressurized fluid indicated as being delivered or injected into manifold or pressure line 85 by arrow 85A.

Figure 17:
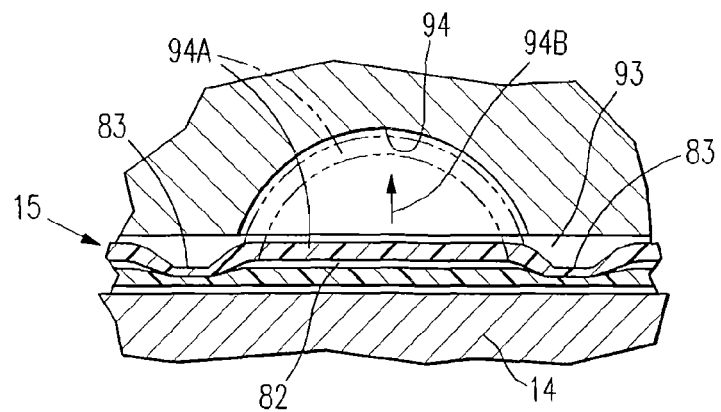
FIG. 17 illustrates an outer layer or layers of fusible material being forced into the mold cavity of a portion of the mold by pressurized fluid as indicated by the dotted line.

FIG. 17 illustrates by the phantom lines how the outer layers 94A of circumferential inflatable channel 82 of the fusible material of a graft body section 15 are expanded into the circumferential channel cavity 94 of mold cavity 93. The direction of the expansion of the outer layers 94A to the position indicated by the phantom lines is indicated by arrow 94B. A cross sectional view of the seams 83 of the circumferential inflatable channel 82 is shown in FIG. 17 as well.

While the graft body section network of inflatable channels 84 is in an expanded state by virtue of pressurized material being delivered or injected into pressure line 85, the entire assembly may be positioned within an oven or other heating device (not shown) in order to bring the fusible material of graft body section 15 to a suitable temperature for an appropriate amount of time in order to fix or sinter the fusible material. In one embodiment, the fusible material is ePTFE and the sintering process is carried out by bringing the fusible material to a temperature of between about 335 and about 380 degrees Celsius; specifically, between about 350 and about 370 degrees Celsius. The mold may then be cooled and optionally quenched until the temperature of the mold drops to about 250 degrees Celsius. The mold may optionally further be quenched (for handling reasons) with ambient temperature fluid such as water. Thereafter, the two halves 91 and 100 of mold 90 can be pulled apart, and the graft assembly removed.

The use of mold 90 to facilitate the inflatable channel expansion and sintering process is unique in that the mold cavity portion 93 acts as a backstop to the graft body section so that during sintering, the pressure created by the injected fluid that tends to expand the inflatable channels outward is countered by the restricting pressure exerted by the physical barrier of the surfaces defining the mold cavity 93. In general terms, therefore, it is the pressure differential across the inflatable channel ePTFE layers that in part defines the degree of expansion of the channels during sintering. During the sintering step, the external pressure exerted by the mold cavity surface competes with the fluid pressure internal to the inflatable channels (kept at a level to counteract any leakage of fluid through the ePTFE pores at sintering temperatures) to provide an optimal pressure differential across the ePTFE membrane(s) to limit and define the shape and size of the inflatable channels.

Based on this concept, we have found it possible to use alternatives to a mold in facilitating the inflatable channel expansion process. For instance, it is possible inject the channel network with a working fluid that does not leak through the ePTFE pores and to then expand the network during sintering in a controlled manner, without any external constraint. An ideal fluid would be one that could be used within the desired ePTFE sintering temperature range to create the necessary pressure differential across the inflatable channel membrane and the ambient air, vacuum, or partial vacuum environment so to control the degree of expansion of the channels. Ideal fluids are those that possess a high boiling point and lower vapor pressure and that do not react with ePTFE, such as mercury or sodium potassium. In contrast, the network of inflatable channels 84 can also be expanded during the fixation process or sintering process by use of vapor pressure from a fluid disposed within the network of inflatable channels 84. For example, the network of inflatable channels 84 can be filled with water or a similar fluid prior to positioning assembly in the oven, as discussed above. As the temperature of the graft body section 15 and network of inflatable channels 84 begins to heat, the water within the network of inflatable channels 84 begins to heat and eventually boil. The vapor pressure from the boiling water within the network of inflatable channels 84 will expand the network of inflatable channels 84 provided the vapor is blocked at the inflation line 85 or otherwise prevented from escaping the network of inflatable channels.

Figure 18:
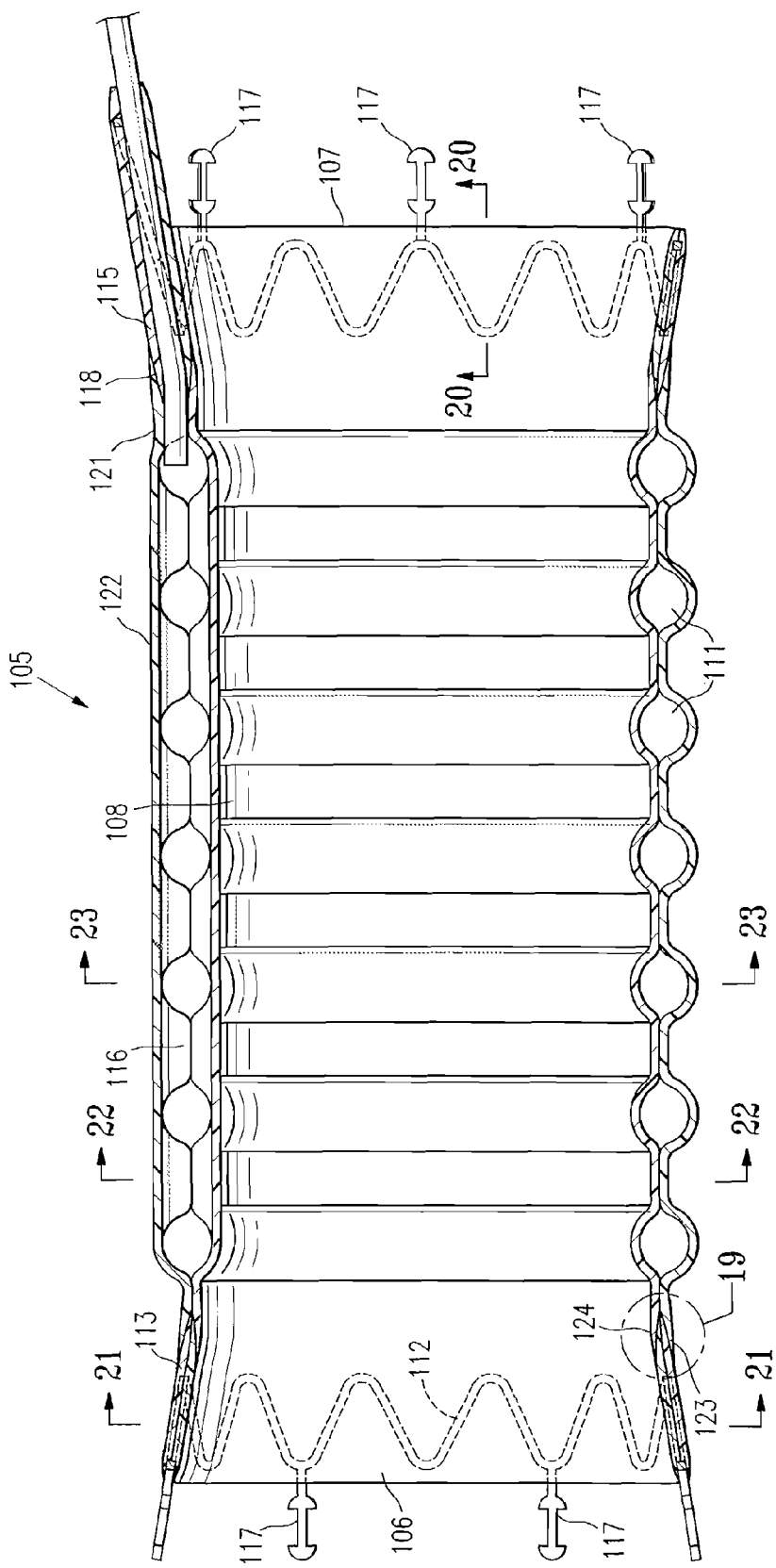
FIG. 18 is an elevational view in partial section of an embodiment of an inflatable endovascular graft of the present invention.

FIG. 18 shows an elevational view in partial longitudinal section of an endovascular graft assembly 105 manufactured by the methods and with the apparatus described above. Endovascular graft assembly 105 comprises a graft body section 108 with a proximal end 106, a distal end 107, and circumferentially oriented inflatable channels 111 shown in an expanded state. A longitudinal inflatable channel 116 fluidly communicates with the circumferential inflatable channels 111.

An expandable member in the form of a proximal connector member 112 is shown embedded between proximal end wrap layers 113 of fusible material. An expandable member in the form of a distal connector member 114 is likewise shown embedded between distal end wrap layers 115 of fusible material. The proximal connector member 112 and distal connector member 114 of this embodiment are configured to be secured or connected to other expandable members which may include stents or the like, which are not shown. In the embodiment of FIG. 18, such a connection may be accomplished via connector elements 117 of the proximal and distal connector members 112 and 114, which extend longitudinally outside of the proximal and distal end wrap layers 113 and 115 away from the graft body section 108.

The FIG. 18 embodiment of the present invention features junction 118 between the distal end wrap layers 115 of fusible material and the layers of fusible material of a distal end 121 of the graft assembly main body portion 122. There is likewise a junction 123 between the proximal end wrap layers 113 and the layers of fusible material of a proximal end 124 of the graft assembly main body portion 122. The junctions 118 and 123 may be tapered, with overlapping portions that are bound by sintering or thermomechanical compaction of the end wrap layers 113 and 115 and layers of the main body portion 122. This junction 123 is shown in more detail in FIG. 19.

Figure 19:
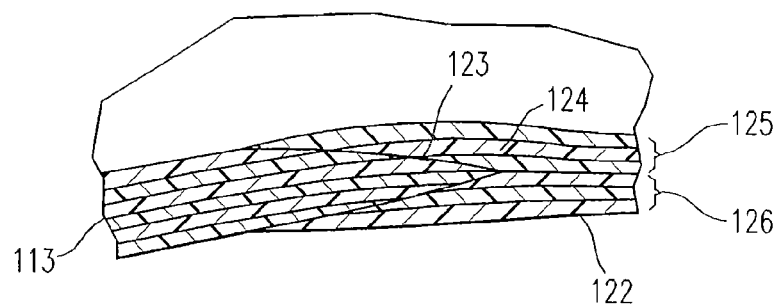
FIG. 19 is an enlarged view of the graft of FIG. 18 taken at the dashed circle indicated by numeral 19 in FIG. 18.

In FIG. 19, six proximal end wrap fusible material layers 113 are disposed between three fusible material inner layers 125 and three fusible material outer layers 126 of the main body portion proximal end 124.

Figure 20:
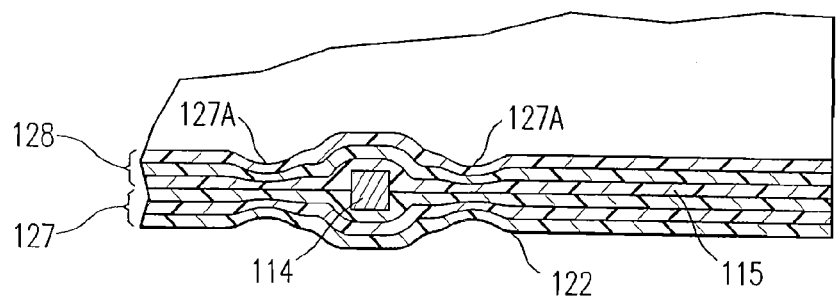
FIG. 20 is an enlarged view in section taken along lines 20-20 in FIG. 18.
Figure 21:
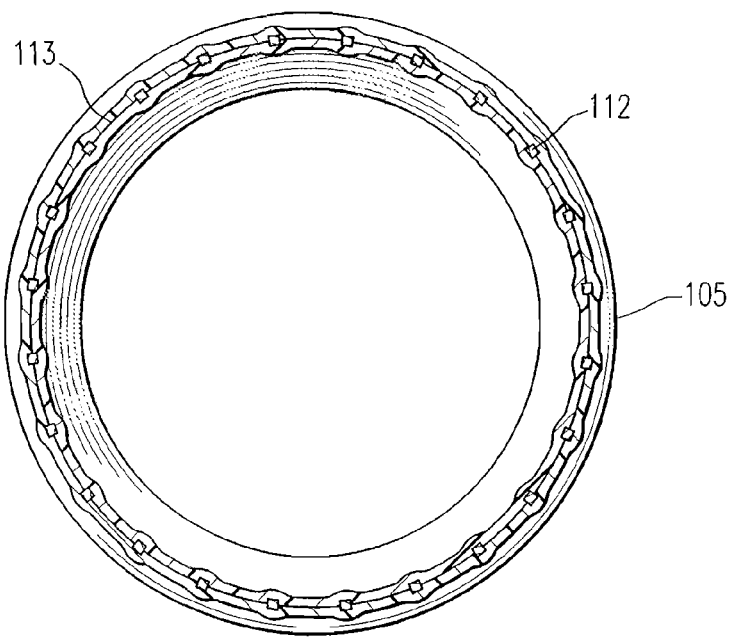
FIG. 21 is a transverse cross sectional view of the graft of FIG. 18 taken along lines 21-21 in FIG. 18.

FIG. 20 illustrates a sectional view of a portion of the distal connector member 114 disposed within the distal end wrap layers 115 of fusible material. Connector member 114 is disposed between three outer layers 127 of fusible material and three inner layers 128 of fusible material. Optional seams 127A, formed by the methods discussed above, are disposed on either side of distal connector member 114 and mechanically capture the connector member 114. FIG. 21 likewise is a transverse cross sectional view of the proximal connector member 112 embedded in the proximal end wrap layers 113 of fusible material.

Figure 22:
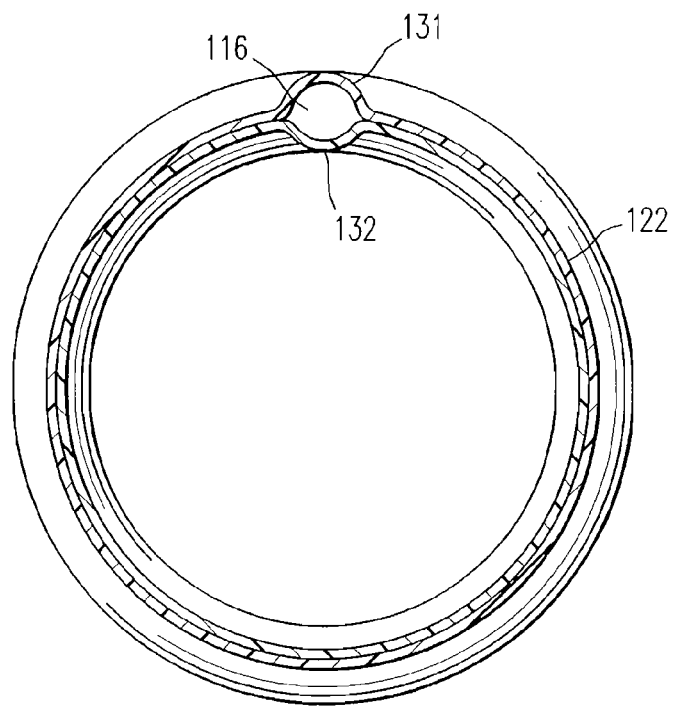
FIG. 22 is a transverse cross sectional view of the graft of FIG. 18 taken along lines 22-22 in FIG. 18.
Figure 23:
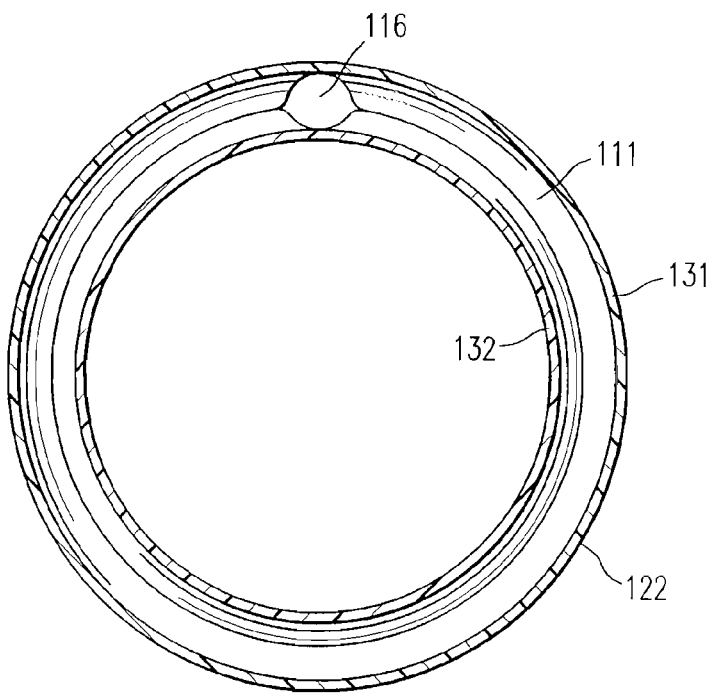
FIG. 23 is a transverse cross sectional view of the graft of FIG. 18 taken along lines 23-23 in FIG. 18.

FIG. 22 illustrates a transverse cross section of the longitudinal inflatable channel 116 formed between main body portion 122 outer layers 131 and the main body portion 122 inner layers 132. FIG. 23 is a transverse cross section of graft main body portion 122 showing a circumferential inflatable channel 111 in fluid communication with longitudinal inflatable channel 116. The circumferential inflatable channel 111 is formed between the outer layers 131 of fusible material of main body portion 122 and inner layers 132 of fusible material of main body portion 122.

Figure 24:
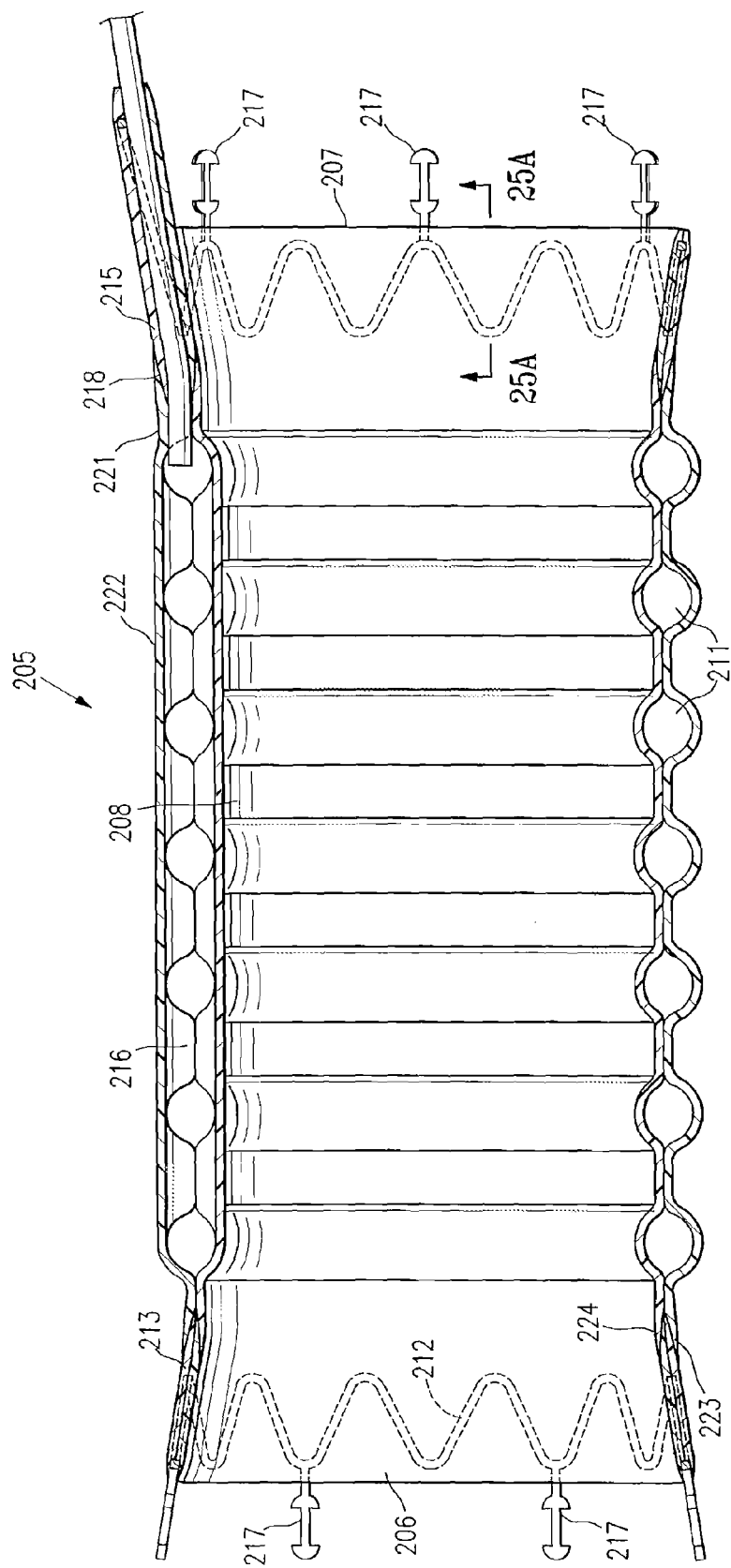
FIG. 24 is an elevational view in longitudinal section of an embodiment of an endovascular graft having features of the invention.

FIG. 24 shows an endovascular graft assembly 205 having a graft body section 208 with a proximal end 206, a distal end 207, and circumferential inflatable channels 211 shown in an expanded state. A proximal connector member 212 is embedded between proximal end wrap layers 213 of flexible material. A distal connector member 214 is embedded between distal end wrap layers 215 of flexible material. The proximal connector member 212 and distal connector member 214 are configured to be connected to other expandable members or stents (not shown). A longitudinal inflatable channel 216 is disposed in fluid communication with the circumferential inflatable channels 211 and extends longitudinally along the graft body section 208. Connector elements 217 of the proximal and distal connector members 212 and 214 extend longitudinally outside of the proximal and distal end wrap layers 213 and 215 away from the graft body section 208.

There is a junction 218 between the distal end wrap layers of flexible material 215 and the layers of flexible material of a distal end 221 of a main body portion 222 of the graft assembly 205. There is also a junction 223 between the proximal end wrap layers 213 and the layers of flexible material of a proximal end 224 of the main body portion 222 of the graft assembly 205. The junctions 218 and 223 may be tapered junctions with overlapping portions as shown. Junctions 218 may be secured by sintering or thermomechanical compaction of the junction if the flexible material consists of a fusible material or the like.

FIG. 25A illustrates a transverse cross section of a portion of the distal connector member 214 disposed within the distal end wrap layers of flexible material 215 and secured to the end wrap layers by a joint 230. Joint 230 includes distal connector member 214, or portion thereof, disposed within a loop portion 231 of a second layer of flexible material 232. The loop portion 231 of the second layer of flexible material 232 is formed by a flap 233 which has been folded back about the distal connector member 214 in a looped configuration and secured to a portion of the second layer of flexible material at a secured portion 234.

A first layer of flexible material 235 is disposed inside and upon an inner surface 236 of the second layer of flexible material 232 and continues distally to the distal end 207 of the graft body section 208. A third layer of flexible material 237 is disposed upon an outside surface 238 of the second layer of flexible material 232 and extends distally to the distal end 207 of the graft body section 208. The first layer of flexible material 235 and third layer of flexible material 237 contact each other and are bonded or secured to each other distal of joint 230. Flap 233 may be secured to the second layer of flexible material 232 by a variety of suitable methods including adhesive bonding, thermomechanical compaction (including, e.g., seam formation, sintering, welding) or the like. The secured portion 234 may also be secured or bonded to the adjacent first layer of flexible material 235 and third layer of flexible material 237 by the same or similar methods. The joint 230 is particularly strong and resistant to forces tending to pull the distal connector member 214 in a distal direction against the end wrap layers 215 being pulled in a proximal direction. The tensile forces of such stress will be distributed into a shear load on the secured portion of the flap 233 which is bonded over a surface area which is large relative to the surface area of the corresponding portion of the distal connector member 214.

FIG. 25B illustrates the joint 230 from outside the graft assembly 205 with the third layer of flexible material 237 not shown to more clearly illustrate the construction of joint 230. FIG. 25B shows flap 233 secured to the second layer of flexible material 232 at the secured portion 234 which extends across the majority of flap 233 as indicated by brackets and hatch lines in FIG. 25B. The loop portion 231 is disposed about the corresponding portion of the distal connector member 214. A void 241 is shown where flap 233 has been cut from the second layer of flexible material 232 against the first layer of flexible material 235.

FIG. 26 shows an alternative embodiment of a joint 245, similar in some respects to the joint 230 of FIG. 24, between a transversely oriented member such as a connector member 246 and end wrap layers of flexible material 247. The connector member 246 is disposed within a loop portion 248 of a third layer of flexible material 249 which is formed by a flap 251 that is folded back upon the third layer of flexible material 249 about the connector member 246. Flap 251 is secured to the third layer of flexible material 249 over a secured portion 252. An additional flap 253 formed from a second layer of flexible material 254 is folded back about the connector member 246, loop portion 248, flap 251 and secured portion 252. Additional flap 253 is secured to flap 251 and third layer of flexible material 254 at an additional secured portion 255.

Proximal of additional flap 253, a fourth layer of flexible material 258 is disposed outside and upon an outside surface 261 of the second layer of flexible material 254 and continues distally to the distal end 207 of the graft body section 208. Proximal of joint 245, a first layer of flexible material 256 is disposed upon an inside surface 257 of the second layer of flexible material 254 and extends distally to the distal end 207 of the graft body section 208. Distal of joint 245, first layer of flexible material 256 and fourth layer of flexible material 258 contact each other and are bonded or secured to each other.

Such a nested joint configuration creates a double layered loop portion 262 which can increase the tensile strength of joint 245 by providing a thicker loop portion 262 which is more resilient to dynamic repetitive loads imposed on the joint. Such a configuration could be extended to include any number of nested loop portions, including 3, 4, 5 or more layers of flexible material formed into a loop portion 248 about a transversely oriented member such as connector member 246.

In the embodiment depicted in FIGS. 25A and 25B, the flap 233 formed from the second layer of flexible material 249 is secured primarily to the same second layer of flexible material 249. However, FIG. 27 illustrates an alternative embodiment of a joint 265 between a connector member 266 and end wrap layers of flexible material 267. Joint 265 has a flap 268 formed from a third layer of flexible material 271 which is folded back on itself about the connector member 266. Flap 268 is secured to a second layer of flexible material 272 which is disposed between the flap 268 and the third layer of flexible material 271. Flap 268 is secured to the second layer of flexible material 272 over a secured portion 273. Proximal of flap 268, a first layer of flexible material 274 is disposed upon an inner surface 275 of the second layer of flexible material 272 and continues distally to the distal end 207 of the graft body section 208. Proximal of joint 265, a fourth layer of flexible material 276 is disposed upon an outside surface 277 of the third layer of flexible material 271 and extends distally to the distal end 207 of the graft body section 208. Distal of joint 265, the first layer of flexible material 274 and fourth layer of flexible material 276 contact each other and are bonded or secured to each other distal of the joint 265.

Figure 28:
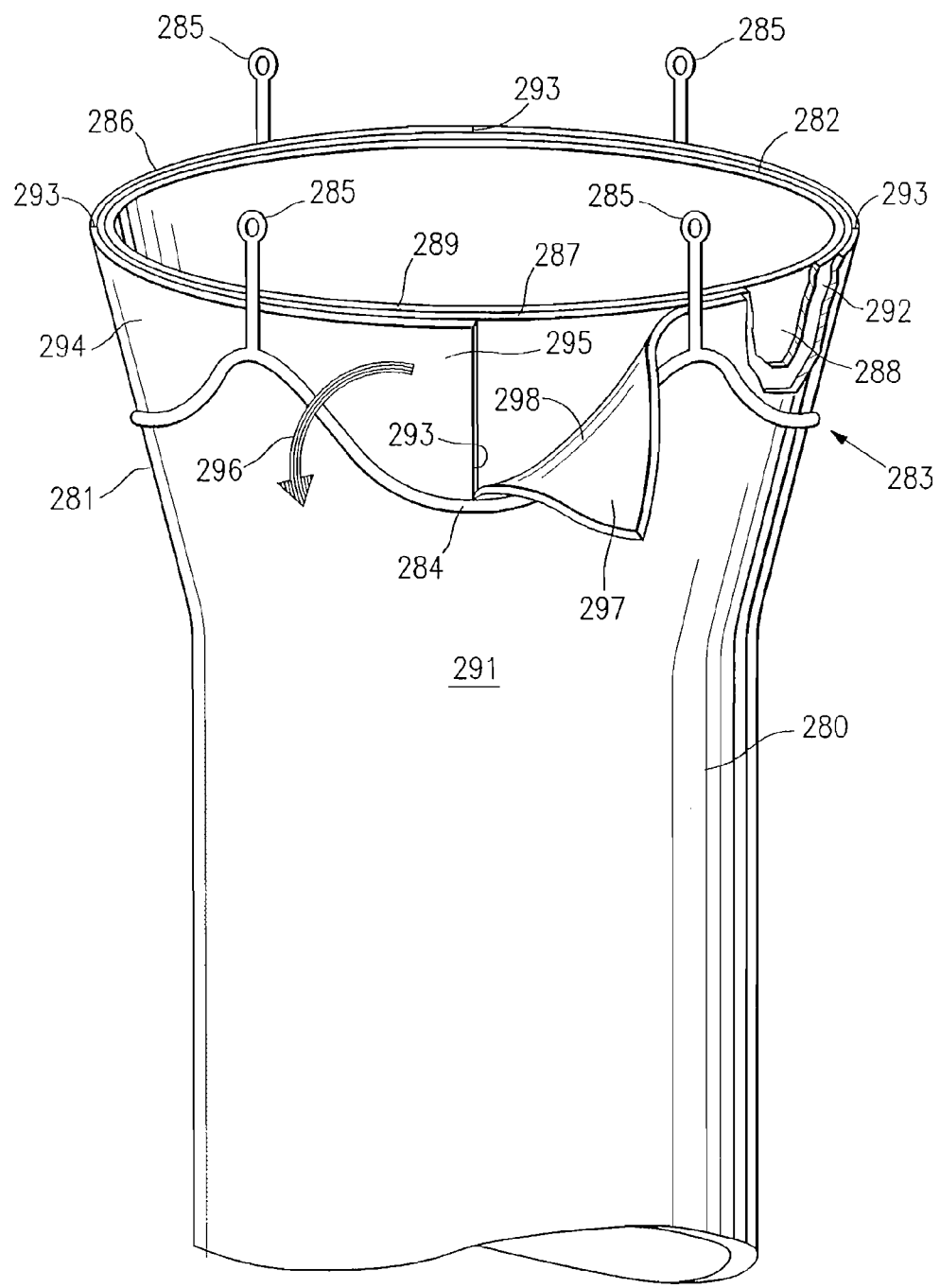
FIG. 28 is a perspective view of a method for manufacturing an endovascular graft wherein a flap of a flexible material portion of the endovascular graft is being formed in a loop about a transversely oriented member.

Referring to FIG. 28, an endovascular graft body section 280 having a generally tubular configuration and a proximal end section 281 which includes proximal end wrap layers of flexible material 282 is shown. A circumferentially oriented member configured as a connector member 283 is disposed about the proximal end wrap layers of flexible material 282 and includes a ring member 284 configured in a serpentine pattern and connector elements 285 extending proximally from the ring member 284 past a proximal end 286 of the graft body section 280.

A second layer of flexible material 287 having a tubular configuration is disposed upon an outside surface 288 of a first layer of flexible material 289 which also has a generally tubular shape. A third layer of flexible material 291 is disposed upon an outside surface 292 of the second layer of flexible material 287. The third layer of flexible material 291 has longitudinal slits 293 formed in a proximal section 294 thereof that extend from the proximal end 286 of the graft body section 280 to ring member 284. A first flap 295 formed from the third layer of flexible material 291 is shown positioned against the outer surface 292 of the second layer of flexible material 287. In order to form a loop portion, the first flap 295 will be folded back on itself in the direction indicated by the arrow 296. A second flap 297 is shown folded back on itself in a loop configuration about the ring member 284 of the connector member 283 to form a loop portion 298.

Figure 29:
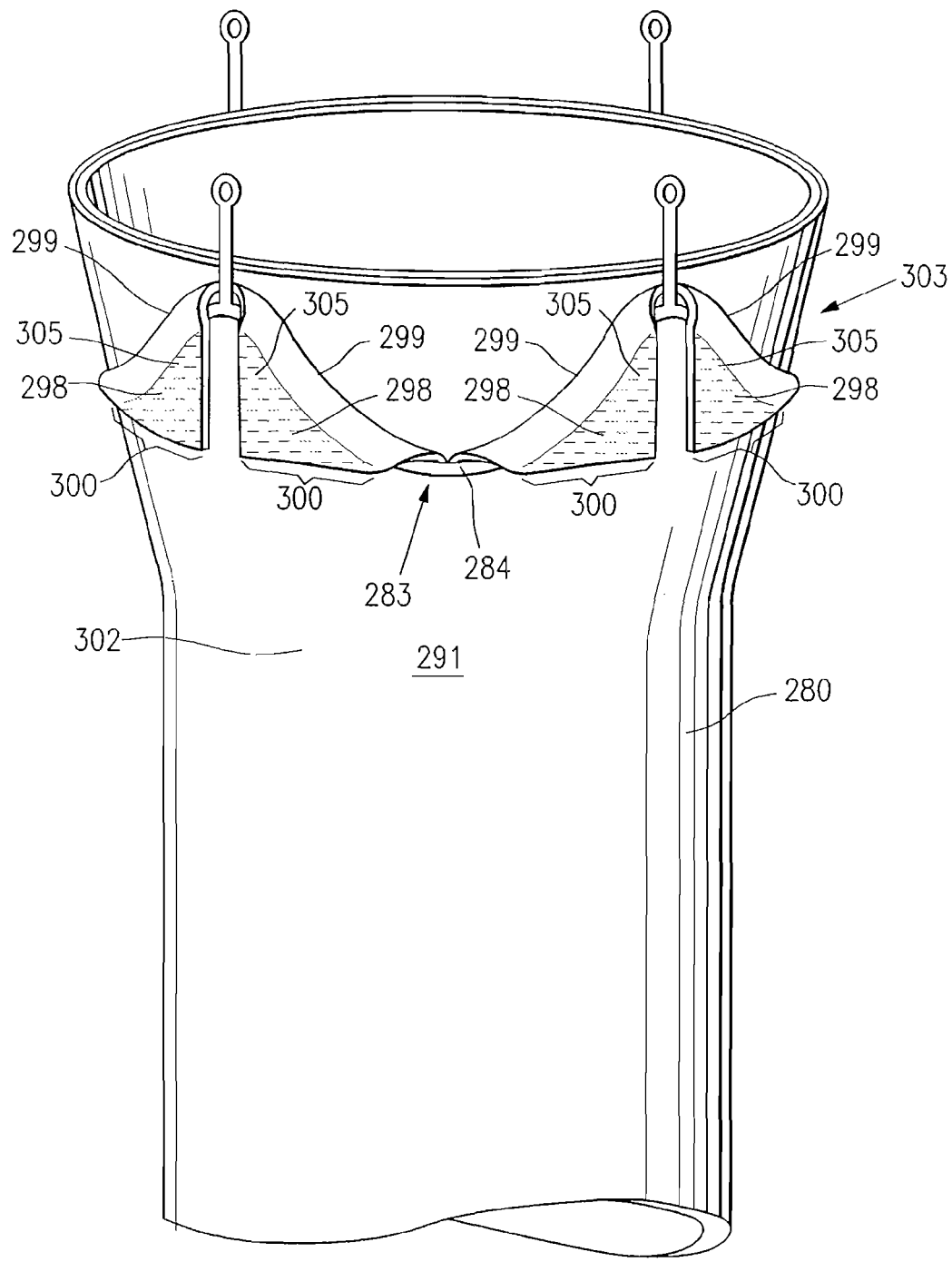
FIG. 29 is a perspective view of the endovascular graft of FIG. 28 with a plurality of flaps of the flexible material portion of the endovascular graft being formed in loops about portions of the transversely oriented member.
Figure 30:
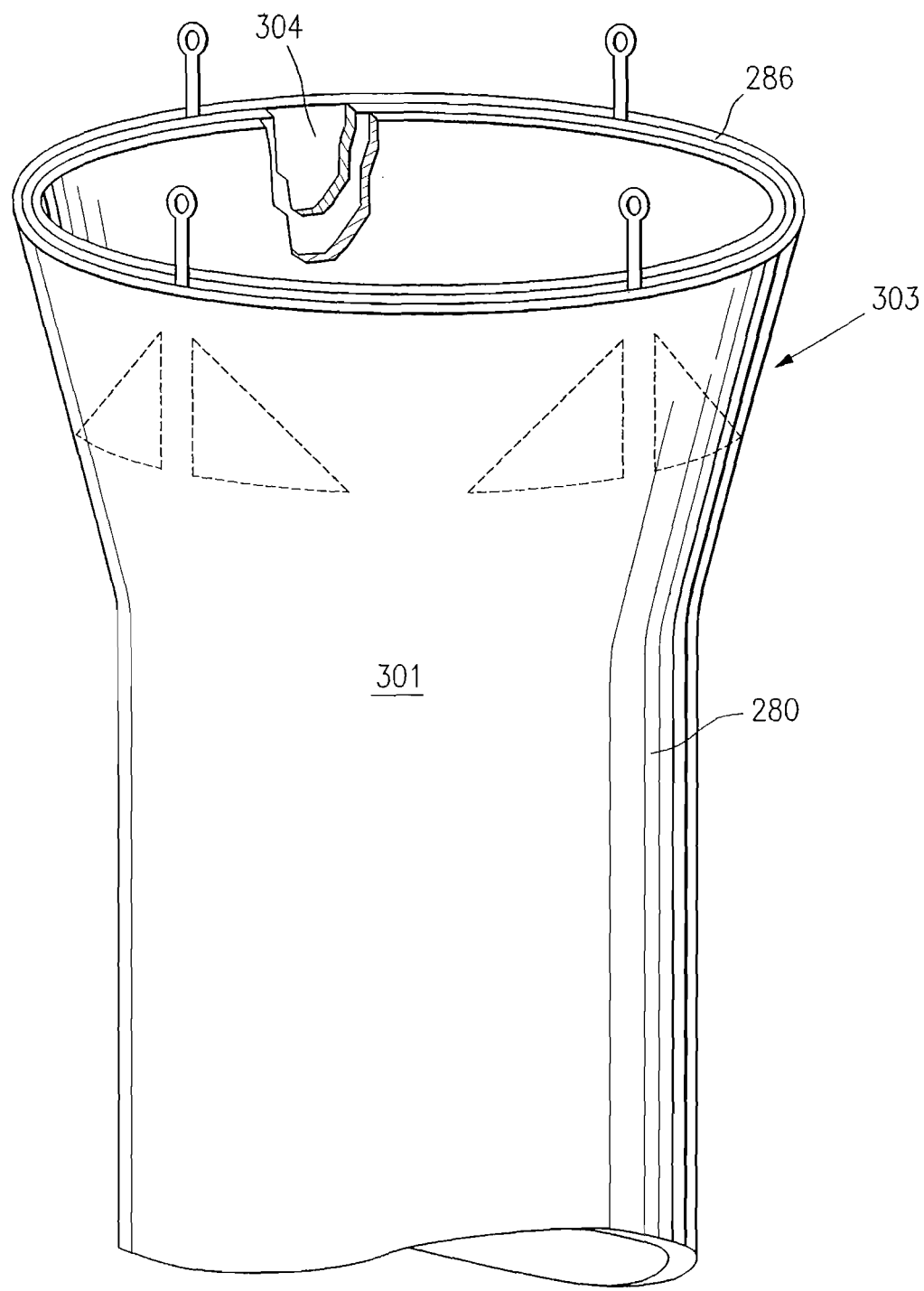
FIG. 30 illustrates a perspective view of the endovascular graft of FIGS. 28 and 29 with an outer layer of flexible material disposed over the flap portions.

In FIG. 29, a plurality of flaps 298 are shown folded back to form loop portions 299 about the ring member 284 of the connector member 283 and such flaps 298 have been folded over the substantial circumference of the ring member 284. Flaps 298 are then secured to the third layer of flexible material 291 over secured portions 300 by any of the methods discussed above. Once flaps 298 are secured, a fourth layer of flexible material 301 is disposed upon an outer surface 302 of the third layer of flexible material 291, the flaps 298, the loop portions 299 and the connector member 283 as shown in FIG. 30. For some embodiments of an endovascular graft body section 280, the number of flaps 298 that are disposed about a connector member 283 can be from about 2 to about 24 flaps. For certain embodiments, the flaps 298 may vary in size from about 1 to about 25 square millimeters.

The fourth layer of flexible material 301 extends to the proximal end 286 of graft body section 280 and may be secured in place by adhesive bonding, sintering, welding, thermomechanical compaction or any other suitable means. In some embodiments, the fourth layer of flexible material 301 may be disposed only over the joint 303 of the graft body section 280. Such a joint 303 secures the connector member 283 to the proximal end wrap layers 282 of graft body section 280 with a joint 303 that is highly resistant to tensile forces between those components. When the fourth layer of flexible material 301 is secured in place, an inside surface 304 of the fourth layer of flexible material 301 may be secured to an outside surface 305 of the flaps 298 in order to further lock the flaps 298 in the loop configuration and further strengthen the joint 303 between the connector member 283 and the end wrap layers 282 of graft body section 280.

Figure 31:
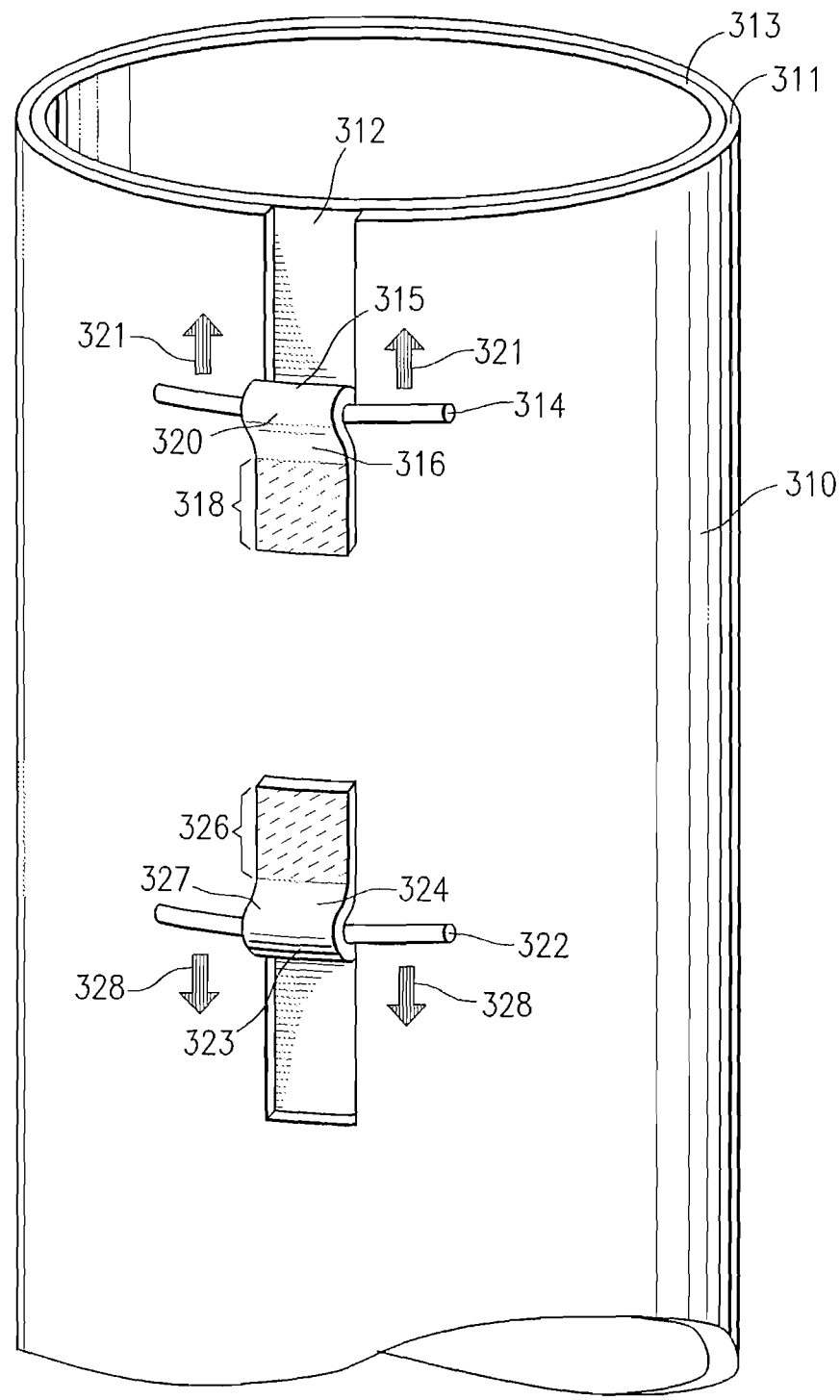
FIG. 31 illustrates a tubular section of an endovascular graft having a first layer of flexible material and a second layer of flexible material wherein flaps of flexible material have been formed in the second layer of flexible material, formed in loop portions about transversely oriented members and secured in a looped configuration about the transversely oriented members.

FIG. 31 shows a graft section 310 having a generally tubular configuration. A second layer of flexible material 311 is disposed upon an outside surface 312 of a first layer of flexible material 313, with both layers having a generally tubular configuration. A first transversely oriented member 314 in the form of a metallic rod is disposed within a loop portion 315 of a flap 316. The flap 316 is formed from a portion of the second layer of flexible material 311 folded back about the first transversely oriented member 314 and is secured to the second layer of flexible material 311 over a secured portion 318 to form a joint 320.

Joint 320 is particularly resistant to tensile forces imposed upon the first transversely oriented member 314 in the direction of the arrows 321. A second transversely oriented member 322 in the form of a metallic rod is disposed within a loop portion 323 of a flap 324. Flap 324 is formed from a portion of the second layer of flexible material 311 folded back about the second transversely oriented member 322 and is secured to the second layer of flexible material 311 over a secured portion 326 to form a joint 327. Joint 327 is particularly resistant to tensile forces imposed upon the first transversely oriented member in the direction of the arrows 328.

FIG. 31 illustrates that the load of any particular tensile force may be dissipated by a joint having certain features of the invention depending on the configuration and orientation of the flap and secured portion of the flap. In the embodiment shown in FIG. 31, opposing tensile forces could be imposed on the first transversely oriented member 314 and the second transversely oriented member 322 and adequately distributed over the respective secured portions 318 and 326 to the extent that the flexible material of the loop portions 315 and 323 of the respective joints 320 and 327 would likely fail prior to the bond at the respective secured portions 318 and 326, depending on the relative tensile strength inherent in the flexible material of the second layer of flexible material 311. This will generally hold true for joints 320 and 327 made with ePTFE, both uniaxial and multiaxial, as the flexible material layer wherein the secured portion is secured by thermomechanical compaction.

While particular forms of embodiments of the invention have been illustrated and described, it will be apparent that various modifications can be made without departing from the spirit and scope of the invention. Accordingly, it is not intended that the invention be limited, except as by the appended claims.

We claim:

1. An endovascular graft comprising:
   a tubular graft body having a proximal end and an opposed distal end and further having a longitudinal axis and a circumferential axis, said tubular graft body comprising a plurality of layers of fusible materials;
   wherein said plurality of layers of fusible materials comprise:
   (i) a base layer of expanded polytetrafluoroethylene having a node and fibril structure with the fibrils oriented primarily in a uniaxial direction substantially aligned with the longitudinal axis or substantially aligned with the circumferential axis; and
   (ii) additional layers of polytetrafluoroethylene disposed about said base layer;
   wherein said graft body comprises an inflatable channel or cuff comprising at least two seams of fusible material among said plurality of layers of fusible materials to define the inflatable channel or cuff disposed between at least two of said plurality of layers of fusible material;
   a transversely oriented member disposed near the proximal end of the tubular graft body; and
   a joint disposed about the transversely oriented member, the joint comprising at least one flap of at least one of the additional layers of polytetrafluoroethylene folded back over the tubular graft body and secured thereto to form a loop portion about the transversely oriented member.

2. The endovascular graft of claim 1, wherein said inflatable channel or cuff is a circumferential channel.

3. The endovascular graft of claim 1, wherein said inflatable channel is a longitudinal channel.

4. The endovascular graft of claim 1, wherein said additional layers of polytetrafluoroethylene comprise expanded polytetrafluoroethylene.

5. The endovascular graft of claim 4, wherein said expanded polytetrafluoroethylene of said additional layers of polytetrafluoroethylene comprises multiaxially oriented fibril expanded polytetrafluoroethylene.

6. The endovascular graft of claim 1, wherein said additional layers of polytetrafluoroethylene comprise porous polytetrafluoroethylene.

7. The endovascular graft of claim 1, wherein the fusible material at said at least two seams is non-expanded polytetrafluoroethylene with a relatively high specific gravity as compared to a relatively low specific gravity of the expanded polytetrafluoroethylene.

8. The endovascular graft of claim 1, wherein said at least two seams are formed by thermal-compaction.

9. The endovascular graft of claim 1, wherein said at least two seams are formed by exertion of pressure from about 100 pounds per square inch to about 6,000 pounds per square inch between said plurality of layers of fusible materials.

10. The endovascular graft of claim 1, wherein said at least two seams are formed by application of heat to said plurality of layers of fusible materials from about 320 degrees Celsius to about 550 degrees Celsius.

11. The endovascular graft of claim 1, wherein said at least two seams further comprise an adhesive.

12. The endovascular graft of claim 1, wherein said at least two seams are impervious to fluid penetration.

13. The endovascular graft of claim 1, wherein the at least one flap is configured to transfer tensile force on the transversely oriented member into a shear component of force on the flap and the tubular graft body.

14. The endovascular graft of claim 1, wherein said fibrils are substantially aligned with the longitudinal axis.

15. The endovascular graft of claim 1, wherein said fibrils are substantially aligned with the circumferential axis.

* * * * *